(12) United States Patent
Haraguchi et al.

(10) Patent No.: US 12,011,243 B2
(45) Date of Patent: Jun. 18, 2024

(54) FORCE SENSE DISPLAY DEVICE AND FORCE SENSE DISPLAY METHOD OF MEDICAL ROBOT SYSTEM

(71) Applicant: RIVERFIELD INC., Tokyo (JP)

(72) Inventors: Daisuke Haraguchi, Tokyo (JP); Yasushi Tanaka, Tokyo (JP); Yuki Furusawa, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 360 days.

(21) Appl. No.: 17/438,779

(22) PCT Filed: Feb. 13, 2020

(86) PCT No.: PCT/JP2020/005584
§ 371 (c)(1),
(2) Date: Sep. 13, 2021

(87) PCT Pub. No.: WO2020/189110
PCT Pub. Date: Sep. 24, 2020

(65) Prior Publication Data
US 2022/0160447 A1 May 26, 2022

(30) Foreign Application Priority Data

Mar. 15, 2019 (JP) ................. 2019-048547

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/25* (2016.02); *A61B 90/37* (2016.02); *A61B 2034/301* (2016.02); *A61B 2090/064* (2016.02)

(58) Field of Classification Search
CPC ... A61B 34/37; A61B 90/37; A61B 2034/301; A61B 2090/064; A61B 2034/2074
See application file for complete search history.

(56) References Cited

U.S. PATENT DOCUMENTS

| 2003/0097060 A1 | 5/2003 | Yanof et al. |
| 2007/0197939 A1 | 8/2007 | Wallace et al. |

(Continued)

FOREIGN PATENT DOCUMENTS

| GB | 2545291 B | * 2/2021 | ............. A61B 34/25 |
| JP | 2005-510289 A | 4/2005 | |

(Continued)

OTHER PUBLICATIONS

Extended European Search Report dated May 16, 2022 in European Application No. 20774616.5.

(Continued)

*Primary Examiner* — Jaime Figueroa
*Assistant Examiner* — Benjamin J Brosh
(74) *Attorney, Agent, or Firm* — Sughrue Mion, PLLC

(57) ABSTRACT

A medical robot system including a memory and a central processing unit that performs operations including receiving measurement signals of forces measured at two or more points on one or both of a surgical tool and a slave device that supports the surgical tool, generating image information for displaying information of the forces as images in association with the two or more points at which the forces are measured, based on the measurement signals, and outputting the image information that is generated to a display device that displays the image information in a second display region of the display device which is different from a first display region of the display device in which information on operation of the surgical tool is displayed.

18 Claims, 23 Drawing Sheets

(51) Int. Cl.
  *A61B 90/00* (2016.01)
  *A61B 34/30* (2016.01)

(56) References Cited

U.S. PATENT DOCUMENTS

| | | | |
|---|---|---|---|
| 2010/0169815 A1* | 7/2010 | Zhao | B25J 9/1633 |
| | | | 606/130 |
| 2015/0313547 A1 | 11/2015 | Quinn et al. | |
| 2017/0181808 A1 | 6/2017 | Panescu et al. | |
| 2017/0215970 A1 | 8/2017 | Quinn et al. | |
| 2018/0250086 A1 | 9/2018 | Grubbs | |
| 2018/0263714 A1 | 9/2018 | Kostrzewski et al. | |
| 2018/0289445 A1* | 10/2018 | Krinninger | A61B 34/70 |
| 2018/0325607 A1 | 11/2018 | Isoda et al. | |
| 2019/0090967 A1* | 3/2019 | Guthart | A61B 1/04 |
| 2019/0110849 A1 | 4/2019 | Inoue | |
| 2019/0321118 A1 | 10/2019 | Genova et al. | |
| 2020/0129239 A1 | 4/2020 | Bianchi et al. | |
| 2020/0215691 A1* | 7/2020 | Saruta | B25J 9/1697 |
| 2020/0289227 A1* | 9/2020 | Jiang | A61B 34/76 |
| 2021/0145526 A1* | 5/2021 | Robinson | A61B 34/35 |

FOREIGN PATENT DOCUMENTS

| | | | | |
|---|---|---|---|---|
| JP | 2007-029232 A | | 2/2007 | |
| JP | 2017-514555 A | | 6/2017 | |
| JP | 2018-158104 A | | 10/2018 | |
| JP | 2019209392 A | * | 12/2019 | B25J 13/00 |
| WO | 2017/122322 A1 | | 7/2017 | |
| WO | 2018/005861 A1 | | 1/2018 | |
| WO | 2018/008106 A1 | | 1/2018 | |
| WO | 2019/023020 A1 | | 1/2019 | |

OTHER PUBLICATIONS

Office Action dated Feb. 8, 2023 from the European Patent Office in EP Application No. 20774616.5.
International Search Report for PCT/JP2020/005584 dated Mar. 17, 2020 [PCT/ISA/210].
Written Opinion for PCT/JP2020/005584 dated Mar. 17, 2020 [PCT/ISA/237].
Notice of Reasons for Refusal Japanese Patent Application 2019-048547 dated Nov. 17, 2020.
Notice of Reasons for Refusal Japanese Patent Application 2019-048547 dated Jan. 12, 2021.
International Preliminary Report on Patentability with the translation of Written Opinion dated Sep. 30, 2021 from the International Bureau in International Application No. PCT/JP2020/005584.

* cited by examiner

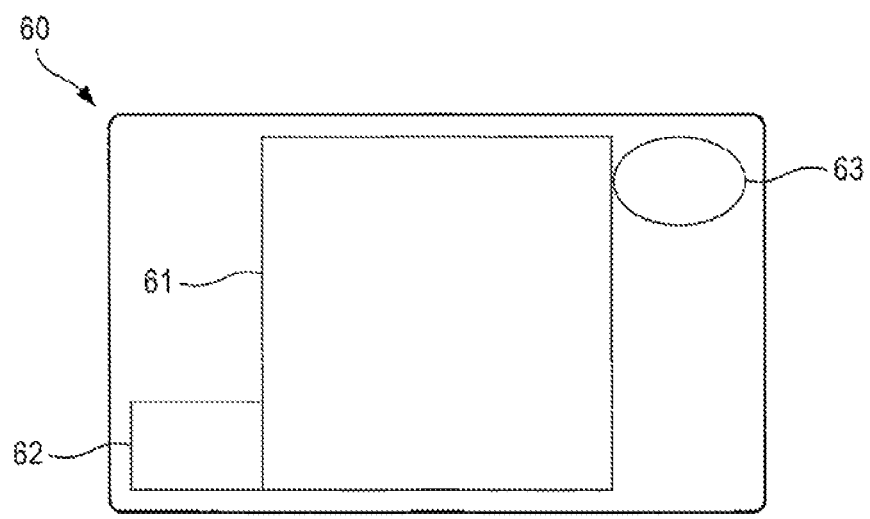

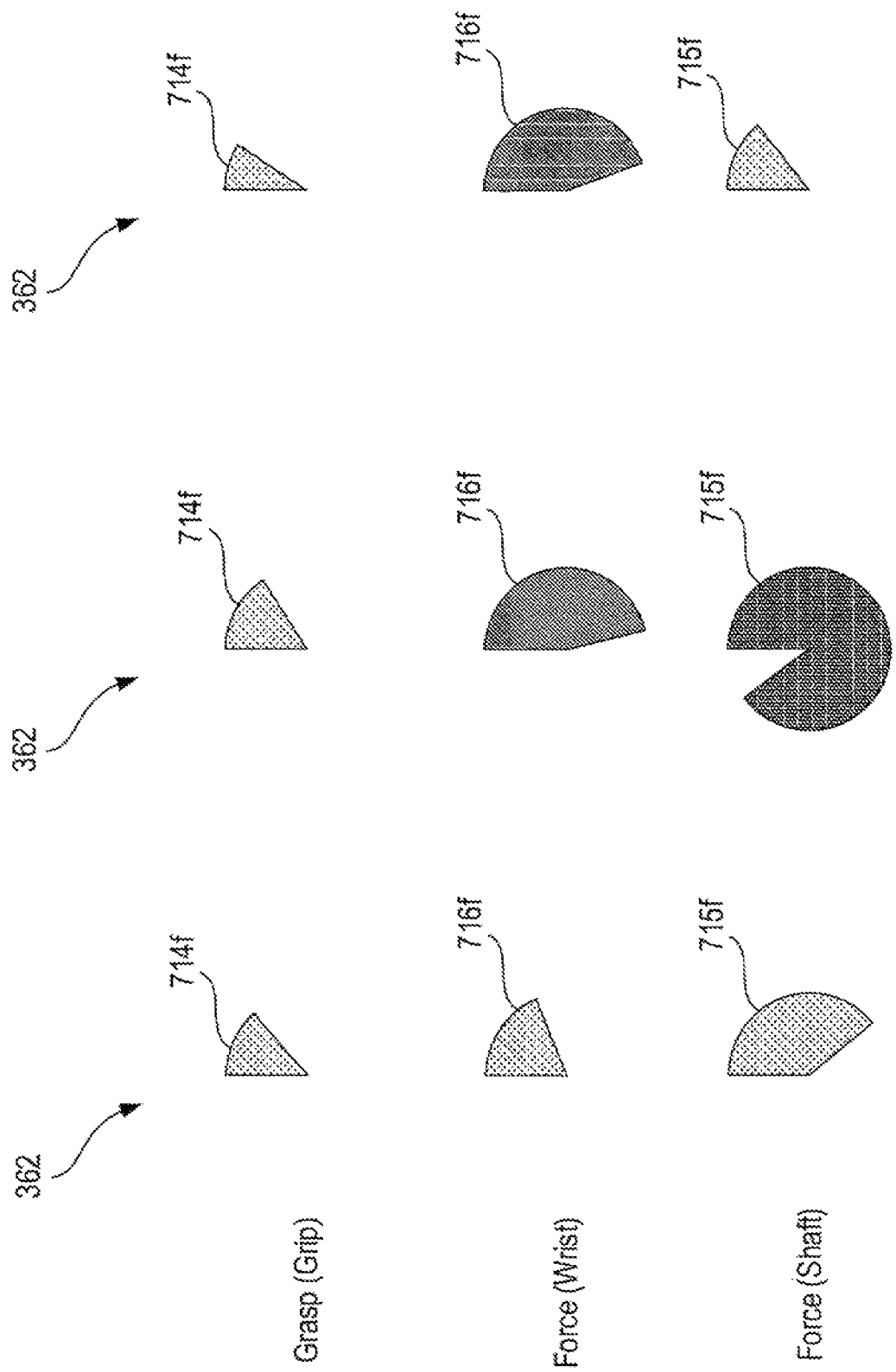

FORCE SENSE DISPLAY DEVICE AND FORCE SENSE DISPLAY METHOD OF MEDICAL ROBOT SYSTEM

CROSS-REFERENCE TO RELATED APPLICATIONS

This application is a National Stage of International Application No. PCT/JP2020/005584 filed Feb. 13, 2020, claiming priority based on Japanese Patent Application No. 2019-048547 filed on Mar. 15, 2019 with the Japan Patent Office, the entire contents of each of which being herein incorporated by reference in their entireties.

TECHNICAL FIELD

The present disclosure relates to a force sense display device and a force sense display method of a medical robot system.

BACKGROUND ART

In recent years, endoscopic surgery using medical robots for surgical assistance is becoming widely available. In endoscopic surgery, surgical tools such as a laparoscope, an endoscope, and forceps, attached to a medical robot are used.

In medical robots, surgical tools can be remotely controlled by a doctor. Also, medical robots that enable intuitive operation are proposed. Further, for the purpose of increasing accuracy and safety, medical robots that can present force sense to transmit an external force acting on a surgical tool to a doctor who operates the medical robot are also proposed (see, for example, Patent Documents 1 and 2).

Patent Document 1 discloses receiving tactile feedback from haptic control in accordance with a measured stress received with a medical device, and displaying the measured stress and the like on a monitor so that the stress applied to a needle is felt.

Patent Document 2 discloses updating a three-dimensional haptic representation based on information generated by tactile feedback. In the following, three dimension will be also referred to as 3D. Specifically, Patent Document 2 describes updating a 3D representation, for example, a 3D graphical representation and/or a 3D haptic representation, of a patient's state when it is determined that a surgical instrument is in contact with a bone of the patient.

PRIOR ART DOCUMENTS

Patent Documents

Patent Document 1: Japanese Unexamined Patent Application Publication No. 2005-510289
Patent Document 2: Japanese Unexamined Patent Application Publication No. 2018-158104

SUMMARY OF THE INVENTION

Problems to be Solved by the Invention

When a method for presenting a force sense is a tactile presentation to the hands of an operating doctor, there is an advantage that the operating doctor can intuitively grasp the force sense. On the other hand, even the same strength of the tactile presentation may be felt differently depending on a doctor receiving the strength, which may lead to lack of accuracy. In addition, since the force sense is presented only to the operating doctor and not to other doctors and the like, it is difficult to perform a third-party real-time check and ensure objectivity.

In a method for displaying the measured stress and the like, in other words, in a method for displaying the force sense, on the monitor, as in the techniques disclosed in Patent Documents 1 and 2, there is an advantage that it is relatively easy to perform the third party real-time check and ensure objectivity as described above. However, since the force sense is displayed on the monitor having a limited area, together with video and image captured by an endoscope or the like, it may be difficult to grasp the force sense. Especially, when two or more different force senses are displayed, difficulty in grasping the force senses becomes remarkable.

In one aspect of the present disclosure, it is preferable to provide a force sense display device and a force sense display method of a medical robot system that can easily increase accuracy and safety of operation in the medical robot system.

Means for Solving the Problems

A force sense display device of a medical robot system in a first aspect of the present disclosure is a device that displays an external force acting on at least one of a surgical tool and a slave device supporting the surgical tool such that the external force is perceptible to an operator. The force sense display device comprises: an input portion configured to receive input of measurement signals of external forces measured at two or more points on at least one of the surgical tool and the slave device; an image generator configured to generate image information for displaying information of the external force as an image in association with the point, at which the external force is measured, in a second display region different from a first display region, in which information on operation of the surgical tool is displayed, based on the measurement signal; and an output portion configured to output the generated image information to a display portion configured to display the image information.

A force sense display method of a medical robot system in a second aspect of the present disclosure is a display method for displaying an external force acting on at least one of a surgical tool and a slave device supporting the surgical tool such that the external force is perceptible to an operator. The force sense display method comprises: receiving input of measurement signals of external forces measured at two or more points on at least one of the surgical tool and the slave device; generating image information for displaying information of the external force as an image in association with the point, at which the external force is measured, in a second display region different from a first display region, in which information on operation of the surgical tool is displayed, based on the measurement signal; and outputting the generated image information to a display portion configured to display the image information.

With the force sense display device in the first aspect and the force sense display method in the second aspect of the present disclosure, it is possible to generate image information for displaying the information of the external force as an image in association with the point at which the external force is measured, and cause the display portion to display the image information. In other words, the information of the external force can be displayed in a manner enabling recognition of the point at which the external force is measured.

Also, since the information of the external force is displayed as an image in the second display region different from the first display region, the displayed information of the external force can be easily grasped, as compared with a case where the information of the external force is displayed in an overlapped manner in the first display region. Further, visibility of information on the surgical tool displayed in the first display region is less likely to be interfered.

In the first aspect of the present disclosure, it is preferable that the image generator generates the image information that represents a magnitude of a value of the external force by at least one of color, shape, and area of the image displayed as the external force.

Since the magnitude of the value of the external force is represented by at least one of the color, shape, and area as such, it becomes easy to intuitively grasp the magnitude of the value of the external force, as compared with a case where the magnitude of the value of the external force is represented by a numerical value.

In the first aspect of the present disclosure, it is preferable that a plurality of slave devices are provided, and the image generator provides a sub-region, inside which the image displayed as the external force is displayed, for each of the slave devices in the second display region.

Thus, inside the sub-region provided for each of the slave devices, the external force measured by the slave device is displayed. Accordingly, it becomes easy to grasp which slave device has measured the external force of the displayed information, even in a case where there are two or more slave devices.

In the first aspect of the present disclosure, it is preferable that the image generator generates the image information that makes it possible to identify the slave device by the shape and hue of at least a part of the sub-region.

Thus, the shape and the hue of at least a part of the sub-region are differentiated among the slave devices. Accordingly, it becomes easy to grasp which slave device has measured the external force of the displayed information.

In the first aspect of the present disclosure, it is preferable that the input portion receives type information indicating a type of the surgical tool grasped by the slave device, and the image generator generates the image information including an image showing a shape of the surgical tool in the sub-region based on the type information.

Since the image showing the shape of the surgical tool grasped by the slave device is displayed in the sub-region as such, it becomes easy to grasp which slave device gripping which surgical tool has measured the external force of the displayed information.

In the first aspect of the present disclosure, it is preferable that the surgical tool is arranged at an end of the slave device that extends in a rod shape, the slave device is provided with a joint that enables change in posture of the surgical tool near the end of the slave device, the measurement signals inputted to the input portion include a joint measurement signal relating to a force acting on the joint and an arm measurement signal relating to external force acting on a part other than the joint in the slave device, and the image generator generates the image information for displaying information on the force acting on the joint and information on the external force acting on the part other than the joint in the slave device based on the joint measurement signal and the arm measurement signal.

Since the information on the force acting on the joint and the information on the external force acting on the part other than the joint in the slave device are displayed as such, it becomes easy to grasp the state of the operating slave device, as compared with a case where the external force acting on a single part is displayed. For example, when the slave devices are brought into contact with each other, the external forces by the contact act on the parts other than the joints (for example, shafts) in the slave devices. Since this information on the external forces is displayed, the operator can grasp that the slave devices are brought into contact with each other.

In the first aspect of the present disclosure, it is preferable that the measurement signals inputted to the input portion include a surgical tool measurement signal relating to a force acting on the surgical tool, and the image generator generates the image information for displaying information on the force acting on the surgical tool based on the surgical tool measurement signal.

Since the information on the force acting on the surgical tool is displayed as such, it becomes easy to grasp an operation state of the surgical tool. For example, when the surgical tool is forceps, a gripping force when closing the forceps to grip and hold an object is displayed. A dissecting force when opening the forceps to dissect the object is also displayed.

Effects of the Invention

With the force sense display device in the first aspect and the force sense display method in the second aspect of the present disclosure, it is possible to generate image information for displaying information of an external force as an image in association with a point, at which the external force is measured, and cause the display portion to display the image information. Thus, there is effect that it becomes easy to increase accuracy and safety of operation in the medical robot system.

BRIEF DESCRIPTION OF THE DRAWINGS

FIG. 5 is a schematic diagram illustrating still another mode of display in the display device of FIG. 1.

FIG. 23 is a schematic diagram illustrating display modes in a first force sense display section, a second force sense display section, and a third force sense display section in a display device of FIG. 22.

Figure 1:
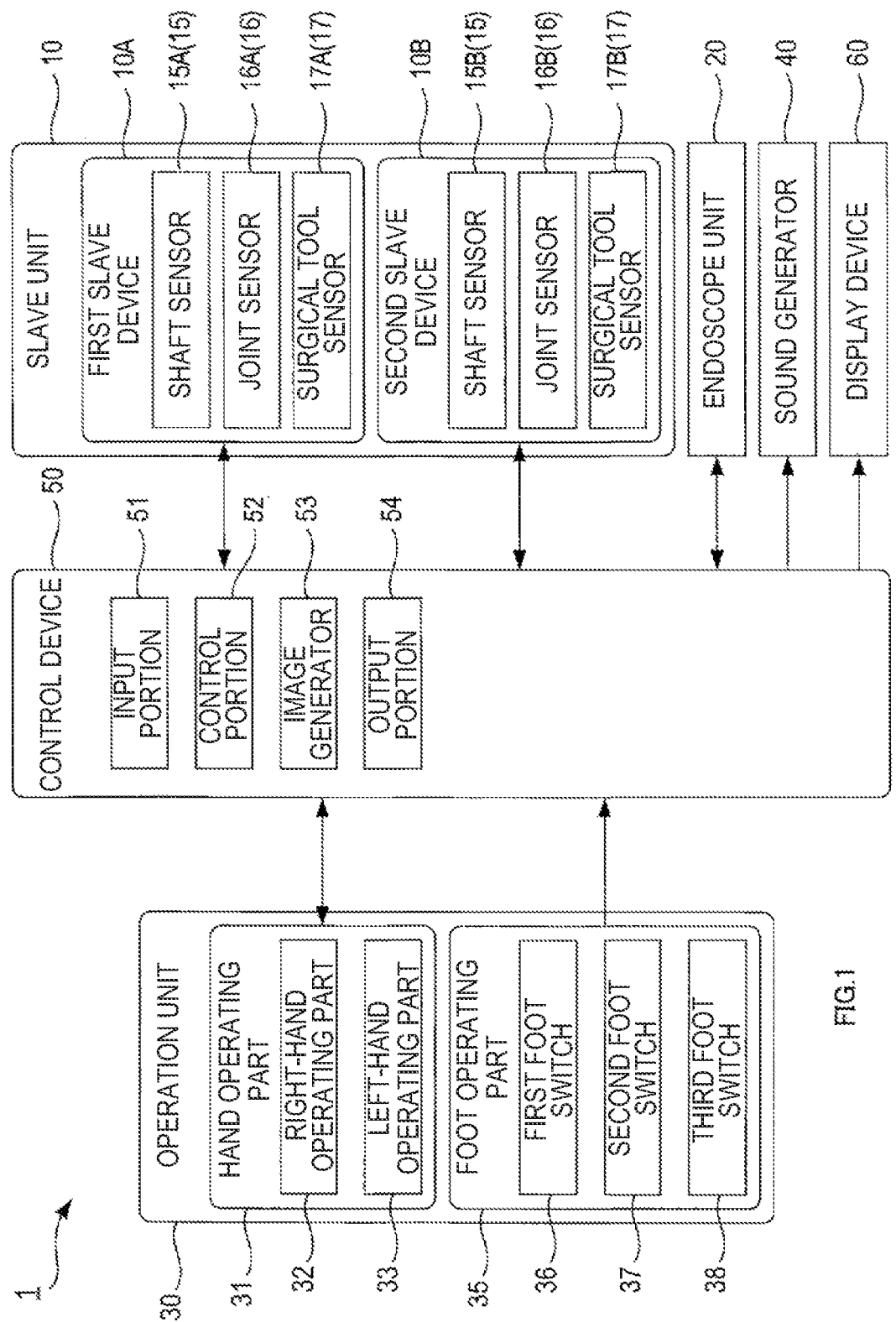
FIG. 1 is a block diagram illustrating a configuration of a medical robot system according to a first embodiment of the present disclosure.

EXPLANATION OF REFERENCE NUMERALS 1, 101, 201, 301, 401, 501, 601, 701 . . . medical robot system, 10, 310 . . . slave unit (slave device), 14 . . . surgical tool, 10A . . . first slave device (slave device), 10B . . . second slave device (slave device), 10C . . . third slave device (slave device), 13 . . . joint, 50, 150, 250, 350, 450, 550, 650, 750 . . . control device (force sense display device), 51 . . . input portion, 53, 153, 253, 353, 453, 553, 653, 753 . . . image generator, 54 . . . output portion, 60 . . . display device (display portion), 61, 361 . . . endoscope image display section (first display region), 62, 162 . . . first force sense display section (second display region), 63, 163 . . . second force sense display section (second display region), 260A . . . first display device (display portion), 260B . . . second display device (display portion), 261 . . . endoscope image display section (first display region), 262 . . . first force sense display section (second display region), 263 . . . second force sense display section (second display region), 362 . . . first force sense display section (sub-region), 363 . . . second force sense display section (sub-region), 364 . . . third force sense display section (sub-region), 365 . . . force sense display section (second display region), S12, S15, S18 . . . input step, S14, S17, S20 . . . image generation step, output step

MODE FOR CARRYING OUT THE INVENTION

First Embodiment

Hereinafter, a medical robot system 1 according to a first embodiment of the present disclosure will be described with reference to FIGS. 1 to 7. The medical robot system 1 of the present embodiment is used for surgical assistance. The medical robot system 1 of the present embodiment is, for example, suitable for use in assisting endoscopic surgery.

The medical robot system 1, as shown in FIG. 1, comprises a slave unit 10, an endoscope unit 20, an operation unit 30, a sound generator 40, a control device 50, and a display device 60. The slave unit 10 corresponds to an example of a slave device, the control device 50 corresponds to an example of a force sense display device, and the display device 60 corresponds to an example of a display portion.

Figure 2:
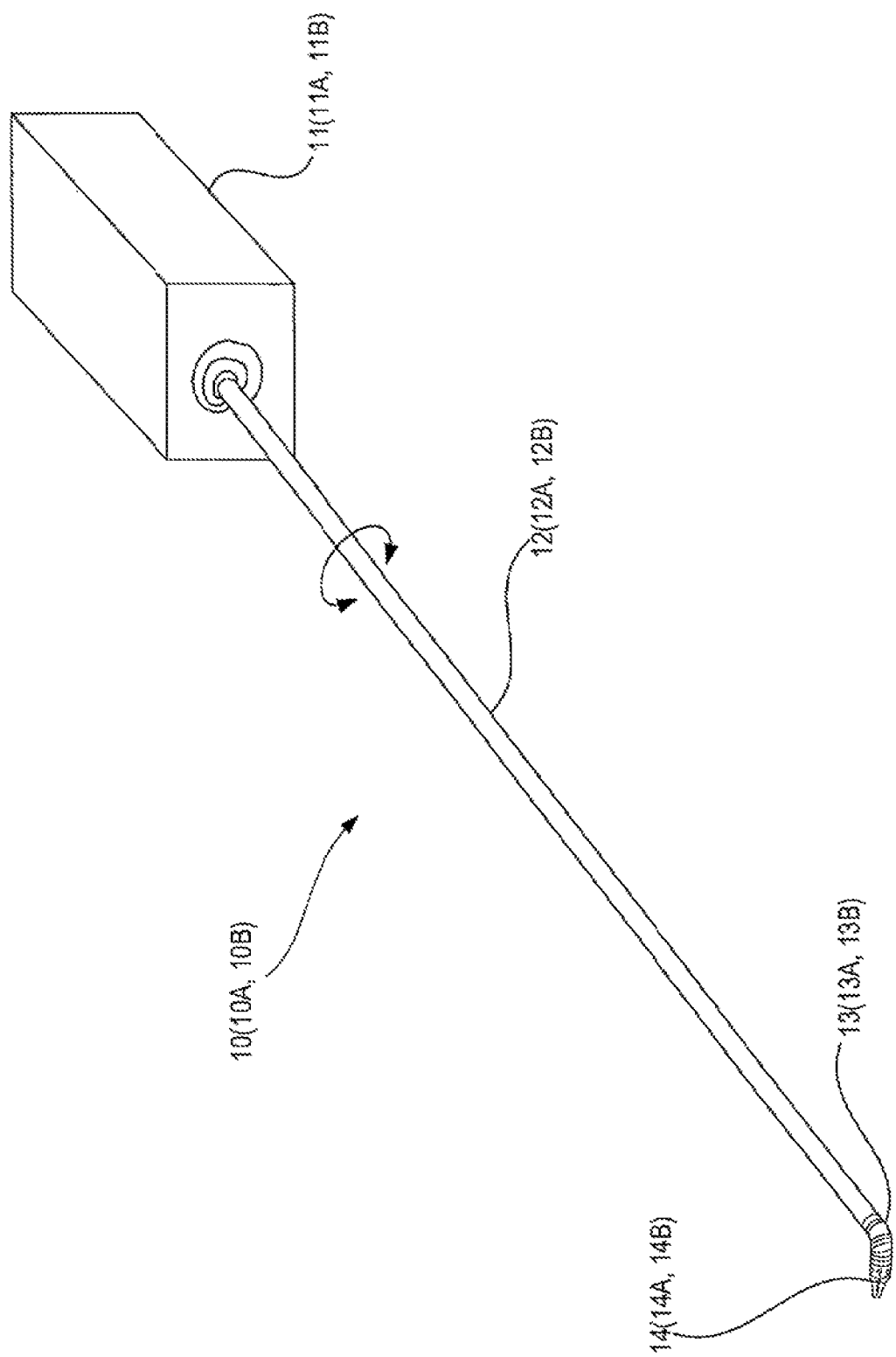
FIG. 2 is a perspective view illustrating a configuration of a cartridge provided in a slave unit of FIG. 1.

The slave unit 10, as shown in FIGS. 1 and 2, supports a surgical tool 14 such as forceps used in endoscopic surgery. Also, the slave unit 10 controls at least one of the position and posture of the surgical tool 14 in accordance with an operation inputted to the operation unit 30. In addition, when the surgical tool 14 is forceps, the slave unit 10 opens and closes the forceps.

In the present embodiment, the slave unit 10 has a first slave device 10A and a second slave device 10B. The slave unit 10 may have more or less than two slave devices. Each of the first slave device 10A and the second slave device 10B corresponds to an example of the slave device.

In the present embodiment, the first slave device 10A and the second slave device 10B are robot arms. Further, the first slave device 10A and the second slave device 10B have the same configuration, and support the same type of surgical tools 14.

The first slave device 10A and the second slave device 10B only need to be able to control at least one of the position and posture of the surgical tool 14, or open and close forceps as the surgical tool 14, and do not have to have an arm-like configuration.

The first slave device 10A and the second slave device 10B, as shown in FIG. 2, are each provided with at least a cartridge 11, a shaft 12, and a joint 13. When it is not necessary to distinguish whether the cartridge 11, the shaft 12, and the joint 13 are provided in the first slave device 10A or in the second slave device 10B, these are referred to as cartridge 11, shaft 12, and joint 13. When it is necessary to distinguish whether the cartridge 11, the shaft 12, and the joint 13 are provided in the first slave device 10A or in the second slave device 10B, these are referred to as cartridge 11A, shaft 12A, and joint 13A, or cartridge 11B, shaft 12B, and joint 13B, respectively.

The cartridge 11 supports the shaft 12, the joint 13, and the surgical tool 14. In the present embodiment, the cartridge 11 has a cubic shape.

The cartridge 11 may store a drive source such as a pneumatic actuator that drives at least one of the shaft 12, the joint 13, and the surgical tool 14. Also, the cartridge 11 may store at least one of a shaft sensor 15 that measures an external force applied to the shaft 12, a joint sensor 16 that measures an external force applied to the joint 13, and a surgical tool sensor 17 that measures opening and closing forces applied to the outside by the forceps as the surgical tool 14.

When it is not necessary to distinguish whether the shaft sensor 15, the joint sensor 16, and the surgical tool sensor 17 are provided in the first slave device 10A or in the second slave device 10B, these sensors are referred to as shaft sensor 15, joint sensor 16, and surgical tool sensor 17. When it is necessary to distinguish whether the shaft sensor 15, the joint sensor 16, and the surgical tool sensor 17 are provided in the first slave device 10A or in the second slave device 10B, these sensors are referred to as shaft sensor 15A, joint sensor 16A, and surgical tool sensor 17A, or shaft sensor 15B, joint sensor 16B, and surgical tool sensor 17B, respectively.

The shaft 12 is a member formed in a cylindrical or columnar shape that extends from the cartridge 11. The shaft 12 is arranged to be rotatable about its central axis with respect to the cartridge 11. The shaft 12 may be formed in a cylindrical or columnar shape, or may be formed in a prismatic shape.

The joint 13 supports the surgical tool 14, and controls the position and posture of the surgical tool 14 by bending. The joint 13 is located between the shaft 12 and the surgical tool 14. In other words, one end of the joint 13 is adjacent to an end of the shaft 12 that is away from the cartridge 11, and the other end of the joint 13 is adjacent to the surgical tool 14. The specific configuration of the joint 13 is not limited as long as the joint 13 is bendable.

The endoscope unit 20, as shown in FIG. 1, acquires video or image for use in performing endoscopic surgery. Specifically, the endoscope unit 20 acquires the video or image of a region within a patient's body cavity subject to surgery. Information of the acquired video or image is outputted to the control device 50. The endoscope unit 20 only needs to be able to output the information of the video or image, and the configuration thereof is not limited.

The operation unit 30 is used for controlling the slave unit 10. Specifically, the operation unit 30 is used when the first slave device 10A and the second slave device 10B are operated to perform endoscopic surgery.

The operation unit 30 comprises a hand operating part 31 and a foot operating part 35. The hand operating part 31 is used when an operator (for example, operator of endoscopic surgery) of the medical robot system 1 inputs movement of the slave unit 10 by hand.

The hand operating part 31 comprises a right-hand operating part 32 corresponding to the right hand of the operator and a left-hand operating part 33 corresponding to the left hand of the operator. The right-hand operating part 32 and the left-hand operating part 33 convert information inputted by the operator to signals and output the signals to a control portion 52. Also, the right-hand operating part 32 and the left-hand operating part 33 present force sense to the operator based on a control signal inputted from the control portion 52.

The configuration and method of the right-hand operating part 32 and the left-hand operating part 33 are not limited. Also, the hand operating part 31 may comprise both the right-hand operating part 32 and the left-hand operating part 33 as described above, or may comprise only one of the right-hand operating part 32 and the left-hand operating part 33.

The foot operating part 35 is used when the operator operates movement and function of the slave unit 10 with foot. The foot operating part 35 comprises a first foot switch 36, a second foot switch 37, and a third foot switch 38. The first foot switch 36, the second foot switch 37, and the third foot switch 38 are operated by the operator stepping on the switches with foot.

Example operations can include supply and stop of high frequency current to the surgical tool 14, switching of a control mode of the slave unit 10, and so on. The type and detail of operation by the foot operating part 35 are not limited. Also, the foot operating part 35 may have three foot switches as described above, or may have less or more than three foot switches.

The sound generator 40 emits sound based on a control signal inputted from the control device 50 to at least some of those involved in endoscopic surgery including the operator. The configuration thereof, such as for generating a sound, is not limited.

The control device 50 controls movement and the like of the slave unit 10, and sound generation in the sound generator 40. The control device 50 controls contents and modes of display displayed on the display device 60.

The control device 50, as shown in FIG. 1, is an information processor such as a computer comprising a CPU, a ROM, a RAM, an input/output interface, and so on. A program stored in a storage device such as the aforementioned ROM causes the CPU, the ROM, the RAM, and the input/output interface to cooperate with each other, and function as at least an input portion 51, the control portion 52, an image generator 53, and an output portion 54. The CPU is an abbreviation for central processing unit.

The input portion 51 receives a signal from the outside. Specifically, the input portion 51 is coupled to the operation unit 30 so that a signal relating to operation can be received, and is coupled to the endoscope unit 20 so that a signal of video and image can be received.

Further, the input portion 51 is coupled to the shaft sensor 15 that measures an external force applied to the shaft 12, the joint sensor 16 that measures an external force applied to the joint 13, and the surgical tool sensor 17 that measures opening and closing forces applied to the outside by the forceps as the surgical tool 14, so that the measurement signals can be received.

The shaft sensor 15, the joint sensor 16, and the surgical tool sensor 17 may be arranged at any location as long as these sensors can measure the external forces as the respective measurement targets, and the locations thereof are not limited. Also, modes for the shaft sensor 15, the joint sensor 16, and the surgical tool sensor 17 to measure the external forces are not specifically limited.

The control portion 52 generates a signal for controlling movements and performance of functions of the slave unit 10 and the surgical tool 14. The control signal is generated based on the signal relating to operation inputted from the operation unit 30.

The image generator 53 generates image information that is information of video and image to be displayed on the display device 60. Specifically, the image generator 53 generates the image information based on the signal of video and image inputted from the endoscope unit 20, and the signals inputted from the shaft sensor 15, the joint sensor 16, and the surgical tool sensor 17. The contents of the image information will be described later.

The output portion 54 outputs the control signal generated in the control portion 52 and the image information generated in the image generator 53. The output portion 54 is coupled to the slave unit 10 and the surgical tool 14 so that the control signal can be outputted to the slave unit 10 and the surgical tool 14, and is coupled to the display device 60 so that the image information can be outputted to the display device 60.

The display device 60 displays video and image based on the image information outputted from the control device 50.

The display device 60 displays the video and image to those involved in surgery including an operator of endoscopic surgery. The method and configuration of the display device 60 are not limited as long as the display device 60 can display video and image.

Next, control in the medical robot system 1 having the above configuration, specifically control relating to force sense will be described. First, a flow of arithmetic processing in the control device 50 will be described with reference to FIG. 3, and then contents to be displayed will be described.

Figure 3:
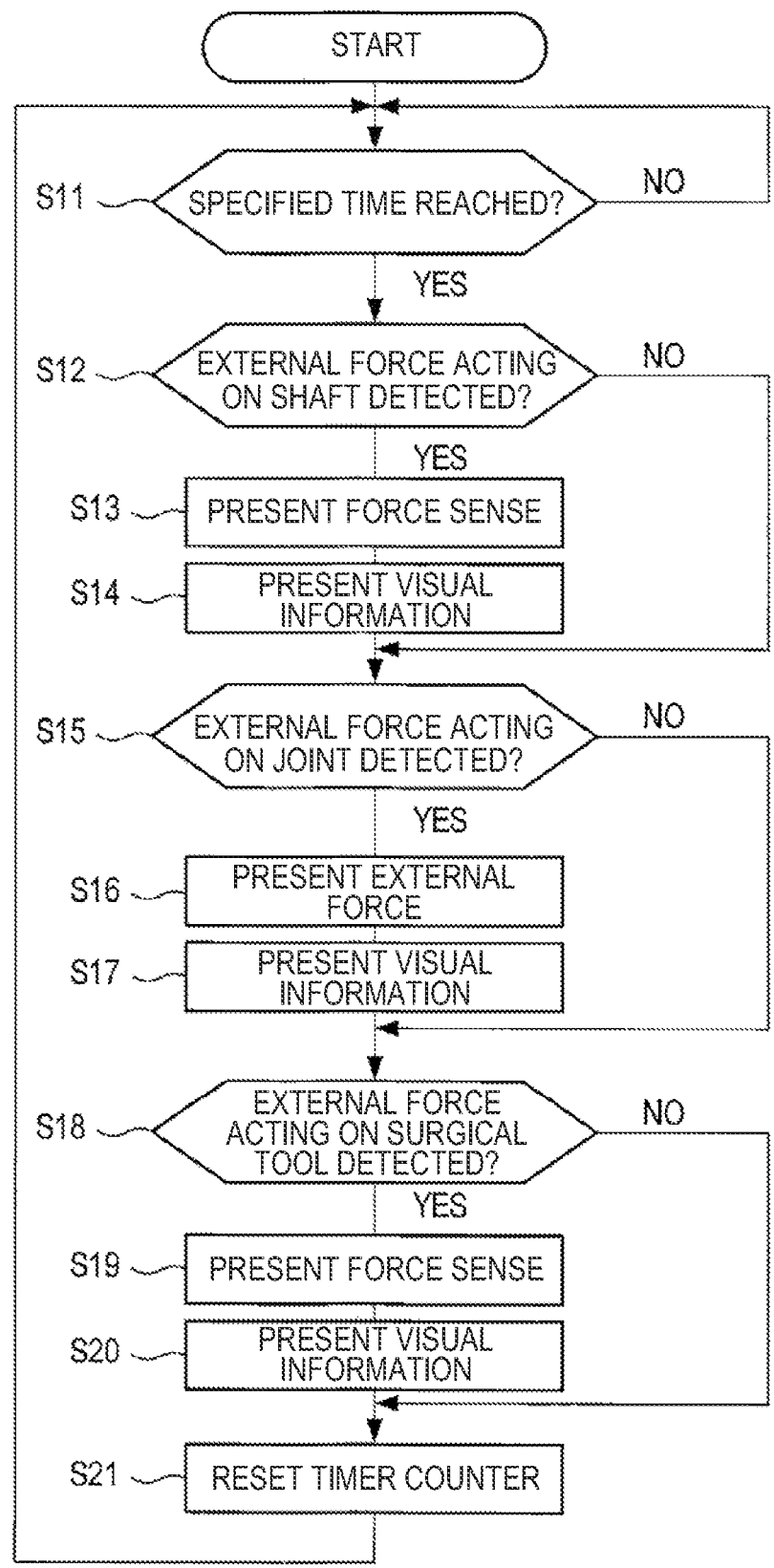
FIG. 3 is a flowchart illustrating control on force sense display in a control device of FIG. 1.

When the control device 50 receives supply of electric power, the control device 50 performs a process to determine whether a timer counter has reached a specified time in S11, as shown in FIG. 3. In the present embodiment, the specified time is 200 ms. The specified time may be 200 ms, as described above, or may be longer or shorter than 200 ms.

When it is determined that the timer counter has not reached the specified time, that is, determined NO, the control device 50 again performs the determination process of S11.

When it is determined that the timer counter has reached the specified time, that is, determined YES, the control device 50 moves the process to an input step of S12. In S12, the control device 50 performs a process to determine whether an external force acting on the shaft 12 is detected. In other words, the control device 50 performs a process to determine whether an arm measurement signal that is a measurement signal of the force is inputted from the shaft sensor 15 to the input portion 51.

) When it is determined that the external force acting on the shaft 12 is detected, that is, determined YES, the control device 50 moves the process to S13. In S13, the control device 50 performs a process to generate a control signal presenting the detected external force as a force sense. The detected external force indicates a magnitude of the force measured by the shaft sensor 15. The detected external force is estimated based on the measurement signal outputted from the shaft sensor 15.

Specifically, a process to make the hand operating part 31 corresponding to a slave device provided with the shaft sensor 15 that has outputted the measurement signal present the detected external force as the force sense is performed. For example, when the shaft sensor 15 that has outputted the measurement signal measures a force acting on the shaft 12 of the first slave device 10A, a process to make the hand operating part 31 (that is, right-hand operating part 32 or left-hand operating part 33) used for operation of the first slave device 10A present the detected external force as the force sense is performed.

Further, a process to set a strength of the force sense to be presented in accordance with the magnitude of the force estimated based on the inputted measurement signal is performed. The corresponding hand operating part 31 presents the force sense corresponding to the force acting on the shaft sensor 15 to the operator based on the control signal outputted from the control device 50.

When the process of S13 is completed, the control device 50 moves the process to an image generation step and an output step of S14. In S14, the control device 50 performs a process to present information on the external force corresponding to the detected external force as information that can be visually grasped. Specifically, the control device 50 performs a process to generate image information for displaying video and image corresponding to the slave device provided with the shaft sensor 15 that has outputted the measurement signal as well as corresponding to the magnitude of the force estimated based on the inputted measurement signal. Detail of the process to generate image information will be described later. The generated image information is outputted to the display device 60. The display device 60 displays the video and image based on the inputted image information.

When the process of S14 is completed, or when it is determined in S12 that the external force acting on the shaft 12 is not detected, that is, determined NO, the control device 50 moves the process to an input step of S15. In S15, the control device 50 performs a process to determine whether an external force acting on the joint 13 is detected. In other words, the control device 50 performs a process to determine whether a joint measurement signal that is a measurement signal of the force is inputted from the joint sensor 16 to the input portion 51.

When it is determined that the external force acting on the joint 13 is detected, that is, determined YES, the control device 50 moves the process to S16. In S16, the control device 50 performs a process to generate a control signal presenting the detected external force as the force sense. The detected external force indicates a magnitude of the force measured by the joint sensor 16. The detected external force is estimated based on the measurement signal outputted from the joint sensor 16.

Specifically, a process to make the hand operating part 31 corresponding to the slave device provided with the joint sensor 16 that has outputted the measurement signal present the detected external force as force sense is performed. Further, a process to set a strength of the force sense to be presented in accordance with the magnitude of the force estimated based on the inputted measurement signal is performed. The corresponding hand operating part 31 presents the force sense corresponding to the force acting on the joint sensor 16 to the operator based on the control signal outputted from the control device 50.

When the process of S16 is completed, the control device 50 moves the process to an image generation step and an output step of S17. In S17, the control device 50 performs a process to present information on the force corresponding to the detected external force as information that can be visually grasped. Specifically, the control device 50 performs a process to generate image information for displaying video and image corresponding to the slave device provided with the joint sensor 16 that has outputted the measurement signal as well as corresponding to the magnitude of the force estimated based on the inputted measurement signal. Detail of the process to generate image information will be described later. The generated image information is outputted to the display device 60. The display device 60 displays the video and image based on the inputted image information.

When the process of S17 is completed, or when it is determined in S15 that the external force acting on the joint 13 is not detected, that is, determined NO, the control device 50 moves the process to an input step of S18. In S18, the control device 50 performs a process to determine whether the external force acting on the surgical tool 14 has been detected. In other words, the control device 50 performs a process to determine whether a surgical tool measurement signal that is a measurement signal of the force is inputted from the surgical tool sensor 17 to the input portion 51.

When it is determined that the external force acting on the surgical tool 14 has been detected, that is, determined YES, the control device 50 moves the process to S19. In S19, the control device 50 performs a process to generate a control signal presenting the detected external force as the force sense. The detected external force indicates a magnitude of the force measured by the surgical tool sensor 17. The magnitude of the force measured by the surgical tool sensor 17 specifically corresponds to a magnitude of a gripping force, or a dissecting force, of the forceps. The detected external force is estimated based on the measurement signal outputted from the surgical tool sensor 17.

Specifically, a process to make the hand operating part 31 corresponding to the slave device provided with the surgical tool sensor 17 that has outputted the measurement signal present the detected external force as the force sense is performed. Further, a process to set a strength of the force sense to be presented in accordance with the magnitude of the force estimated based on the inputted measurement signal is performed. The corresponding hand operating part 31 presents the force sense corresponding to the force acting on the surgical tool sensor 17 to the operator based on the control signal outputted from the control device 50.

When the process of S19 is completed, the control device 50 moves the process to an image generation step and an output step of S20. In S20, the control device 50 performs a process to present information on the force acting on the surgical tool corresponding to the detected external force as information that can be visually grasped. Specifically, the control device 50 performs a process to generate image information for displaying video and image corresponding to the slave device provided with the surgical tool sensor 17 that has outputted the measurement signal as well as corresponding to the magnitude of the force estimated based on the inputted measurement signal. Detail of the process to generate image information will be described later. The generated image information is outputted to the display device 60. The display device 60 displays the video and image based on the inputted image information.

When the process of S20 is completed, the control device 50 moves the process to S21. In S21, the control device 50 performs a process to reset the timer counter to zero (0). When the reset process is completed, the control device 50 returns to S11, and performs the aforementioned process repeatedly. For example, at least while endoscopic surgery is assisted by the medical robot system 1, the aforementioned process is repeatedly performed.

Figure 4A:
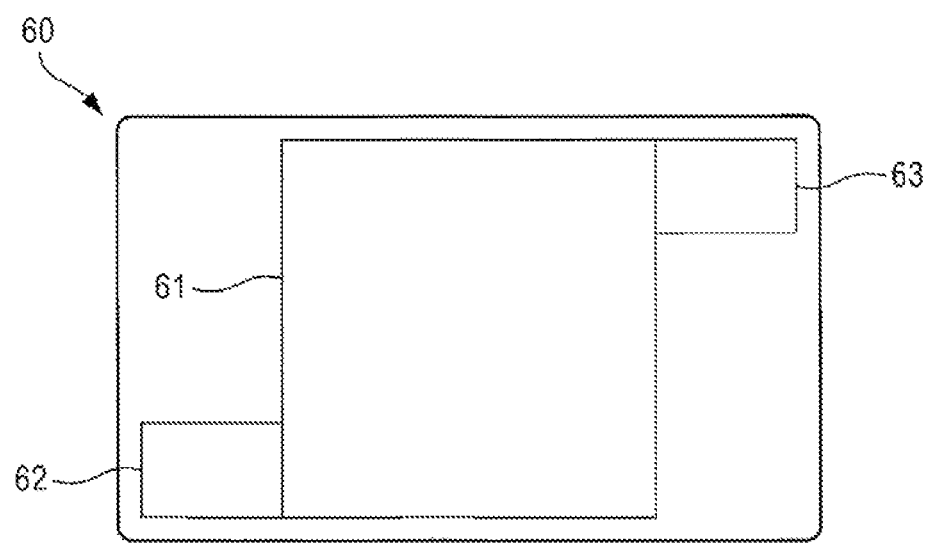
FIG. 4A is a schematic diagram illustrating a mode of display in a display device of FIG. 1.

Next, the image information generated in the image generator 53 will be described. Specifically, a mode of display in the display device 60 will be described. FIG. 4A is a schematic diagram illustrating the mode of display by the display device 60 based on the image information generated by the image generator 53 of the present embodiment.

The image generator 53, as shown in FIG. 4A, sets an endoscope image display section 61 in the center of a right-left direction on a display surface in the display device 60, and sets a first force sense display section 62 in the lower left and a second force sense display section 63 in the upper right of the endoscope image display section 61. The endoscope image display section 61 corresponds to an example of a first display region. The first force sense display section 62 and the second force sense display section 63 each correspond to an example of a second display region.

The endoscope image display section 61 is a region having a wider area than the first force sense display section 62 and the second force sense display section 63. The image generator 53 generates image information that makes the endoscope image display section 61 display the information of the video or image inputted from the endoscope unit 20.

The first force sense display section 62 and the second force sense display section 63 are regions having narrower areas than the endoscope image display section 61. The image generator 53 generates the image information based on the signals inputted from the shaft sensor 15, the joint sensor 16, and the surgical tool sensor 17.

The first force sense display section 62 and the second force sense display section 63 are partitioned from other regions by frames. Also, displays are performed based on the signals inputted from the shaft sensor 15, the joint sensor 16, and the surgical tool sensor 17 inside the partitioned areas in the first force sense display section 62 and the second force sense display section 63. The first force sense display section 62 and the second force sense display section 63 of the present embodiment have frames of the same color formed in the same rectangular shape. Display modes in the first force sense display section 62 and the second force sense display section 63 will be described later.

In the present embodiment, the first force sense display section 62 is a region where display is performed based on the signals inputted from the shaft sensor 15, the joint sensor 16, and the surgical tool sensor 17 corresponding to the first slave device 10A. The second force sense display section 63 is a region where display is performed based on the signals inputted from the shaft sensor 15, the joint sensor 16, and the surgical tool sensor 17 corresponding to the second slave device 10B.

The first force sense display section 62 may be a region where display is performed based on the signals inputted from the shaft sensor 15, the joint sensor 16, and the surgical tool sensor 17 corresponding to the second slave device 10B, and the second force sense display section 63 may be a region where display is performed based on the signals inputted from the shaft sensor 15, the joint sensor 16, and the surgical tool sensor 17 corresponding to the first slave device 10A.

Figure 4B:
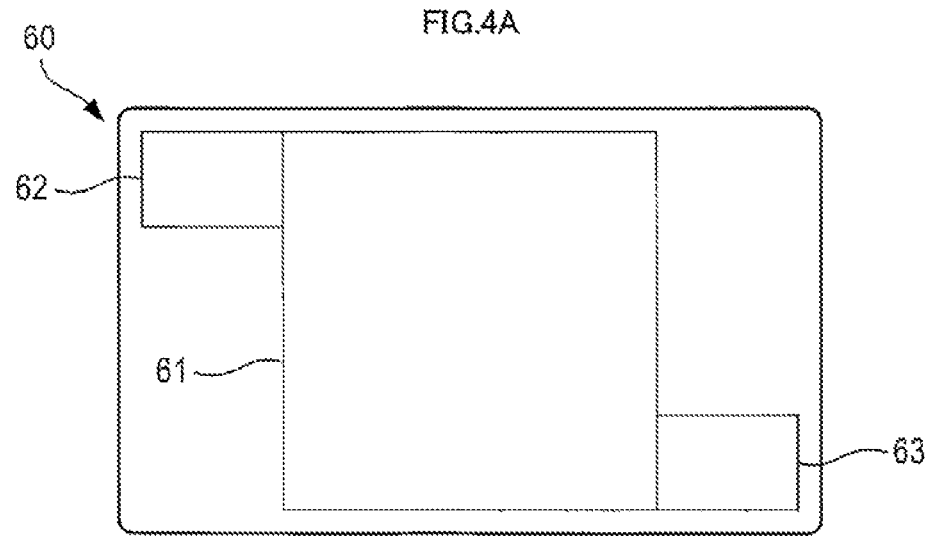
FIG. 4B is a schematic diagram illustrating another mode.
Figure 4C:
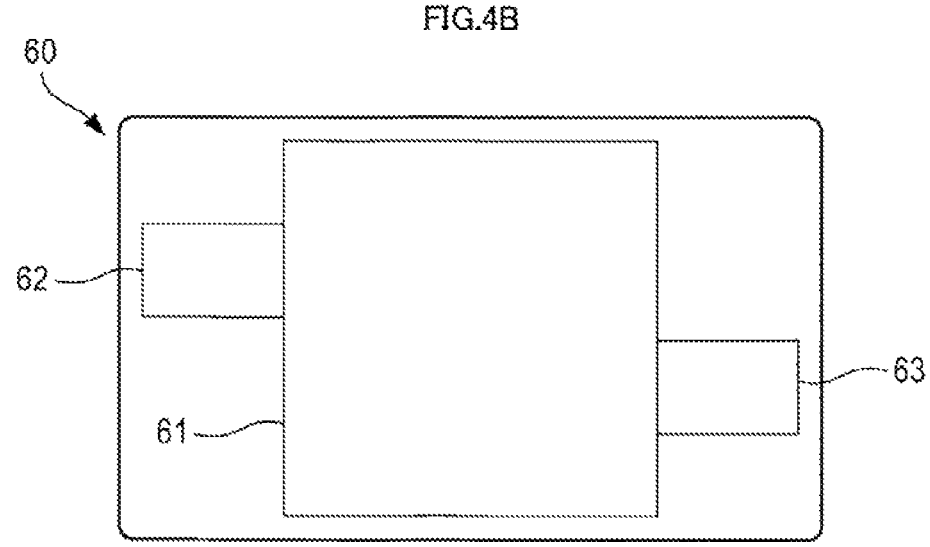
FIG. 4C is a schematic diagram illustrating yet another mode.

In the present embodiment, the first force sense display section 62 is located in the lower left, and the second force sense display section 63 is located in the upper right, of the display surface in the display device 60. Alternatively, as shown in FIG. 4B, the first force sense display section 62 may be located in the upper left, and the second force sense display section 63 may be located in the lower right, of the display surface. Or, as shown in FIG. 4C, the first force sense display section 62 may be located slightly above the left side center, and the second force sense display section 63 may be located slightly below the right side center, of the display surface.

In the present embodiment, the first force sense display section 62 and the second force sense display section 63 are described to have frames in the same color and formed in the same rectangular shape, as an example. Alternatively, the first force sense display section 62 and the second force sense display section 63 may have frames formed in different shapes. For example, as shown in FIG. 5, the first force sense display section 62 may have a frame formed in a rectangular shape, and the second force sense display section 63 may have a frame formed in an oval shape.

Further in the present embodiment, the first force sense display section 62 and the second force sense display section 63 are described to have frames in the same color, as an example. Alternatively, the first force sense display section 62 and the second force sense display section 63 may have frames in different colors.

Next, the display modes in the first force sense display section 62 and the second force sense display section 63 will be described. Since the display modes in the first force sense display section 62 and the second force sense display section 63 are the same, the display mode in the first force sense display section 62 will be described as a representative example, and the description of the display mode in the second force sense display section 63 is omitted. Also, the first force sense display section 62 and the second force sense display section 63 may display the names of the first slave device 10A and the second slave device 10B to facilitate distinguishing between the first force sense display section 62 and the second force sense display section 63.

Figure 6:
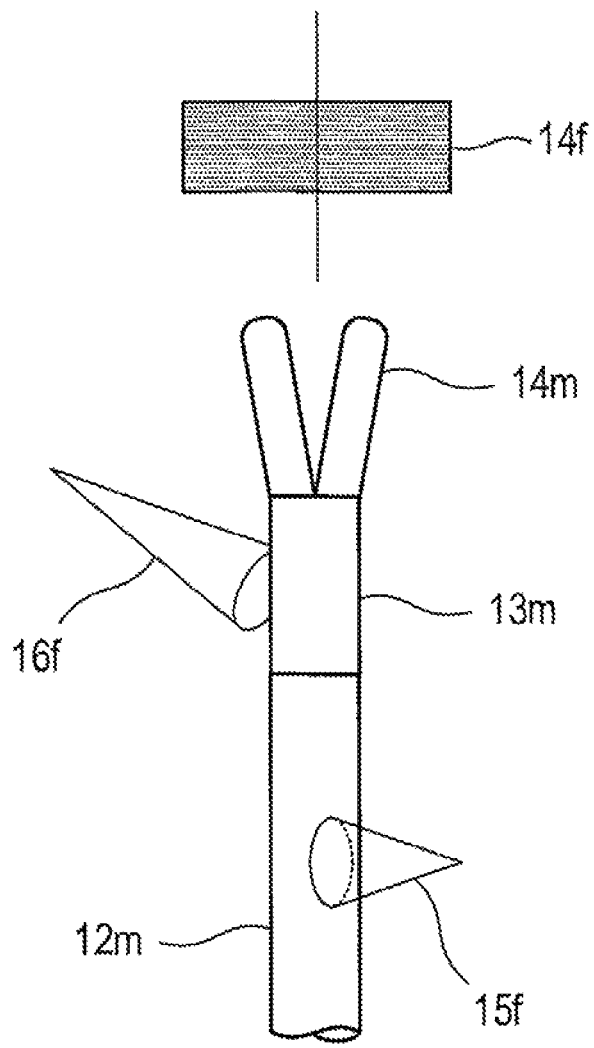
FIG. 6 is a schematic diagram illustrating a display mode in a force sense display section.

The display mode of the first force sense display section 62 is as shown in FIG. 6. In other words, in the first force sense display section 62, three-dimensional models of the shaft 12, the joint 13, and the surgical tool 14 of the first slave device 10A are displayed. In other words, a three-dimensional model of shaft 12m, a three-dimensional model of joint 13m, and a three-dimensional model of surgical tool 14m are displayed. The displayed three-dimensional models reflect an actual posture of the shaft 12, and an actual bent state of the joint 13.

The shape of the surgical tool 14m in the three-dimensional model is determined based on type information indicating the type of the surgical tool 14 inputted via the input portion 51. The control device 50 stores the type information indicating the type of the surgical tool 14 and the shape of the surgical tool 14m in the displayed three-dimensional model associated with each other. The image generator 53 acquires information of the shape of the surgical tool 14m associated with the inputted type information, and generates the image information for displaying the three-dimensional model.

The type information inputted via the input portion 51 may be information inputted such as by a worker that performs settings of the medical robot system 1 or an operator that performs endoscopic surgery, or may be a detection signal outputted from a sensor that detects the type of the attached surgical tool 14.

In a part of the shaft 12m in the three-dimensional model, a conical shape 15f showing the magnitude of the force and a direction of the force is displayed based on the signal inputted from the shaft sensor 15. Also, in a part of the joint 13m in the three-dimensional model, a conical shape 16f showing the magnitude of the force and a direction of the force is display based on the signal inputted from the joint sensor 16.

In the present embodiment, a distance from the bottom surface to an apex of the conical shape corresponds to the magnitude of the force. Also, color in which the conical shape is displayed is changed in accordance with the magnitude of the force. For example, as the force increases, the color is changed among green, yellow, and red. Further, in the present embodiment, a direction from the bottom surface toward the apex of the conical shape indicates the direction of the force.

In a region adjacent to the surgical tool 14 in the three-dimensional model, for example, in a region adjacent to a leading end of the surgical tool 14, a band-like shape showing a magnitude of the force to close or open the forceps as the surgical tool 14 is displayed based on the signal inputted from the surgical tool sensor 17.

Figure 7A:
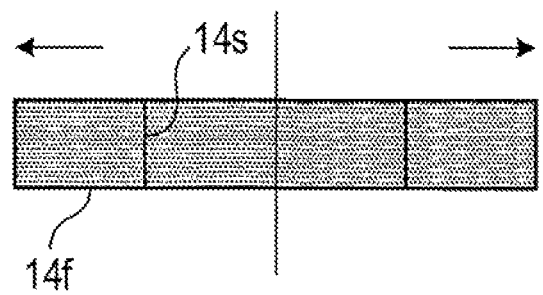
FIG. 7A is a diagram illustrating a dissection display mode.
Figure 7B:
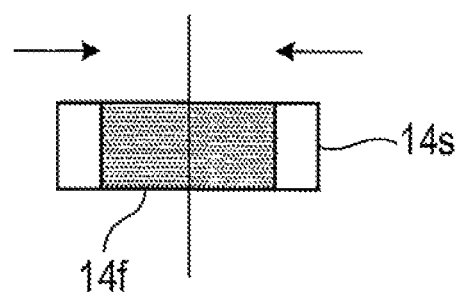
FIG. 7B is a diagram illustrating a grip display mode.

In the present embodiment, as shown in FIG. 7A, the force to open the forceps as the surgical tool 14 is represented by a display in a dissection display mode in which a length of a band-like shape 14f is longer than a preset reference index 14s. Also, as shown in FIG. 7B, the force to close the surgical tool 14 is represented by a display in a grip display mode in which the length of the band-like shape 14f is shorter than the reference index 14s.

Also, difference in length between the band-like shape 14f and the reference index 14s is changed depending on the magnitude of the force, and the magnitude of the force is displayed by the difference in length. For example, when the force increases, the difference in length is displayed to be larger, and, when the force decreases, the difference in length is displayed to be smaller.

Figure 7C:
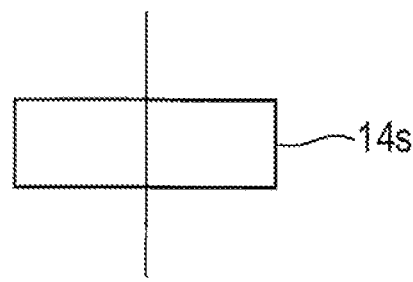
FIG. 7C is a diagram illustrating a display mode when force is not measured.

Alternatively, color of the band-like shape 14f may be changed in accordance with the magnitude of the force. For example, as the force increases, the color is changed among green, yellow, and red. When the force is not measured by the surgical tool sensor 17, the band-like shape 14f is displayed with the same length as the reference index 14s, and in white, as shown in FIG. 7C.

With the control device 50 having the above configuration, it is possible to generate the image information for displaying the information of the external force as an image in association with the point at which the external force is measured, and display the image information on the display device 60. In other words, information of the displayed external force can be displayed in a manner that a point where the external force has been measured is identifiable.

Also, the information of the external force is displayed as an image in the first force sense display section 62 and the second force sense display section 63 which are different from the endoscope image display section 61. Accordingly, the displayed information of the external force can be easily grasped, as compared with a case where the information of the external force is displayed over the endoscope image display section 61. Further, visibility of the forces acting on the shaft 12, the joint 13, and the surgical tool 14 displayed in the endoscope image display section 61 is less likely to be interfered.

The magnitude of the value of the external force is represented by at least one of the color, shape, and area. Therefore, as compared with a case where the magnitude of the value of the external force is represented by a numerical value, it becomes easy to grasp the magnitude of the value of the external force intuitively.

The information on the force acting on the joint 13 and the external force acting on the shaft 12 which is a part other than the joint 13 in the first slave device 10A and the second slave device 10B is displayed. Thus, as compared with a case where the external force acting on a single part (for example, the joint 13 only) is displayed, it becomes easy to grasp the operation states of the first slave device 10A and the second slave device 10B.

For example, when the first slave device 10A and the second slave device 10B are brought into contact with each other, an external force by the contact acts on a part (for example, shafts 12) of the first slave device 10A and the second slave device 10B other than the joints 13. Since the information on this external force is displayed, the operator can grasp that the first slave device 10A and the second slave device 10B are brought into contact with each other.

The information of the forces to open the forceps and close the forceps is displayed as the information on the force acting on the surgical tool 14. Thus, it becomes easy to grasp the operation state of the surgical tool 14. Here, the force to open the forceps is also represented as a dissecting force, and the force to close the forceps is also represented as a gripping force.

The images showing the shapes of the surgical tools 14 gripped by the first slave device 10A and the second slave device 10B are displayed. Thus, it becomes easy to grasp whether the displayed information of the external force is information of the external force measured in the first slave device 10A, or information of the external force measured in the second slave device 10B.

As above, whether the information is on the gripping force or the dissecting force is displayed by changing the length of the band-like shape 14f in comparison with the reference index 14s. Thus, visual recognition of the information becomes easy. Also, since a magnitude of a difference between the length of the band-like shape 14f and the reference index 14s is displayed as a magnitude of the gripping force or the dissecting force, visual recognition of the magnitude of the gripping force or the dissecting force is easy.

As above, since the color or hue of the band-like shape 14f is changed based on the magnitude of the force measured by the surgical tool sensor 17, it becomes easy to grasp the magnitude of the force in the surgical tool 14. Thus, it becomes easy to grasp the magnitude of the displayed gripping force and dissecting force.

First Variation of First Embodiment

Next, a medical robot system according to a first variation of the first embodiment of the present disclosure will be described with reference to FIGS. 8 and 9. The medical robot system of the present variation has a basic configuration similar to that of the first embodiment, but differs from the first embodiment in that there is no endoscope unit. Accordingly, for the present variation, those related to the display of force sense will be described with reference to FIGS. 8 and 9, and other descriptions are omitted.

Figure 8:
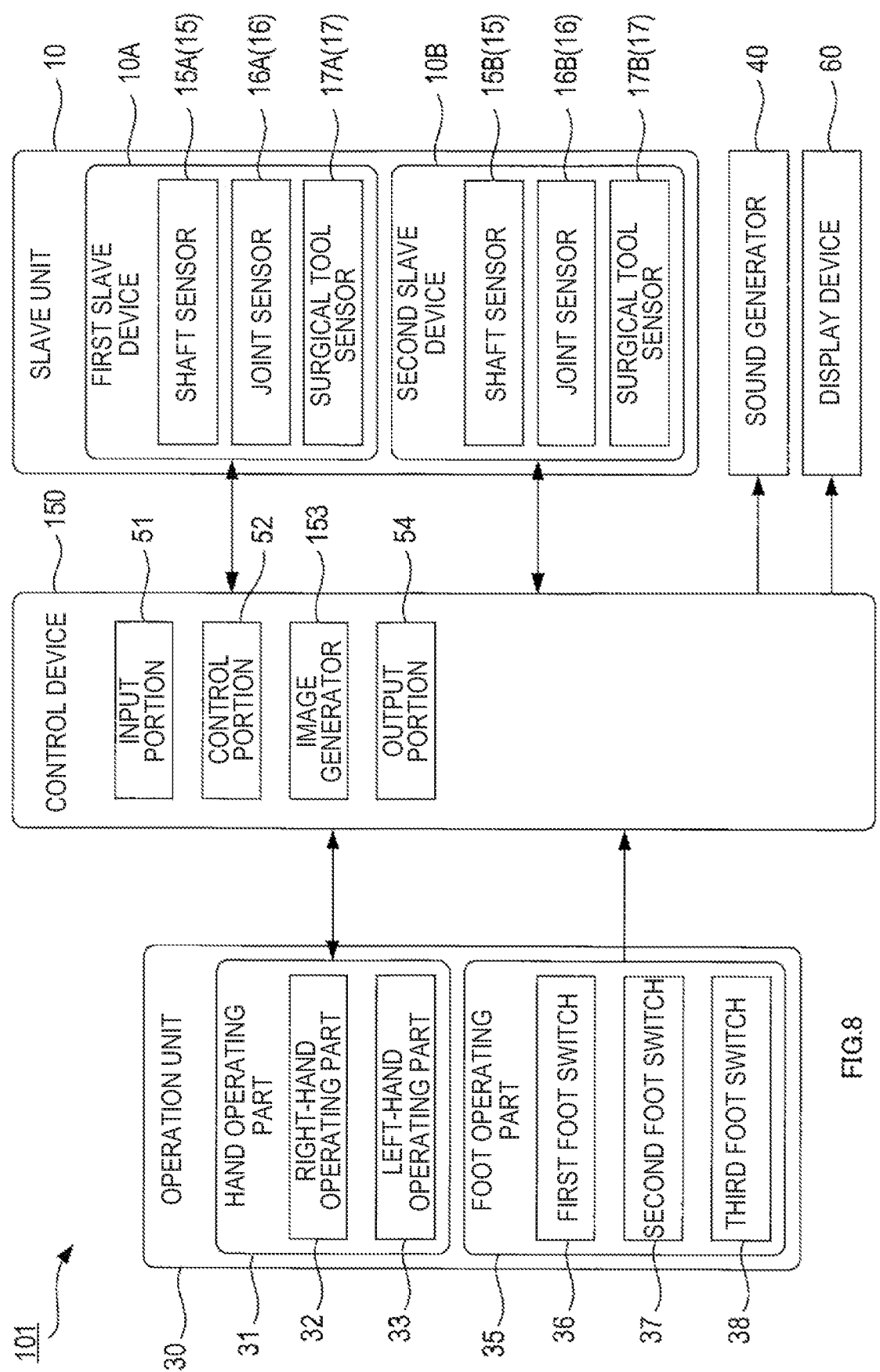
FIG. 8 is a block diagram illustrating a configuration of a medical robot system according to a first variation of the first embodiment of the present disclosure.

A medical robot system 101 of the present variation comprises the slave unit 10, the operation unit 30, the sound generator 40, a control device 150, and the display device 60, as shown in FIG. 8. The control device 150 corresponds to an example of the force sense display device.

The control device 150 controls operation and the like of the slave unit 10 and sound generation in the sound generator 40, and controls contents and modes of the display displayed on the display device 60.

The control device 150, as shown in FIG. 8, is an information processor such as a computer comprising a CPU, a ROM, a RAM, an input/output interface, and the like. A program stored in a storage device, such as the aforementioned ROM, causes the CPU, the ROM, the RAM, and the input/output interface to cooperate with each other, and function as at least the input portion 51, the control portion 52, the image generator 153, and the output portion 54.

The image generator 153 generates image information that is information of video and image to be displayed on the display device 60. Specifically, the image generator 153 generates the image information based on signals inputted from the shaft sensor 15, the joint sensor 16, and the surgical tool sensor 17. The image generator 153 differs from the image generator 53 of the first embodiment in that the image generator 153 does not generate the image information based on the signal of video and image inputted from the endoscope unit 20.

Next, control in the medical robot system 101 having the above configuration will be described. Control by the control device 150 regarding the display of force sense is similar to the control in the first embodiment, and thus the description thereof is omitted.

The image information generated in the image generator 153 will now be described. Specifically, description on the mode of display in the display device 60 will be given. FIG. 9 is a schematic diagram illustrating the mode of display by the display device 60 based on image signal generated by the image generator 153 of the present variation.

Figure 9:
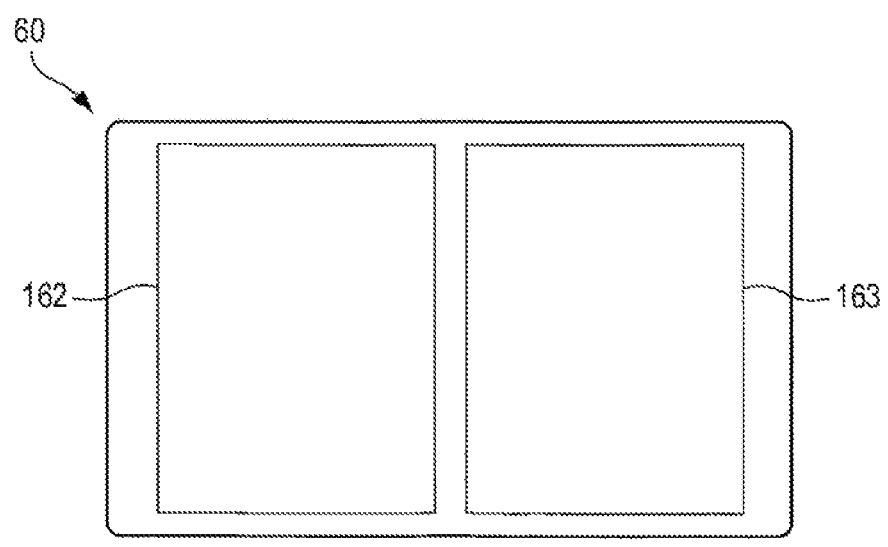
FIG. 9 is a schematic diagram illustrating a mode of display in a display device of FIG. 8.

The image generator 153, as shown in FIG. 9, arranges a first force sense display section 162 on the left side and a second force sense display section 163 on the right side, on the display surface of the display device 60 which is divided into left and right. In other words, as compared with the first embodiment, the present variation differs in that the endoscope image display section 61 is not arranged on the display surface of the display device 60. The first force sense display section 162 and the second force sense display section 163 correspond to an example of the second display region.

In the present variation, an example of dividing the display surface into left and right is described, but the display surface may be divided into upper and lower sides. The mode of dividing the display surface is not limited. In the present variation, the first force sense display section 162 has a display area equal to a display area of the second force sense display section 163. Alternatively, the first force sense display section 162 may have a smaller or larger display area than the display area of the second force sense display section 163.

Further, in the present variation, the first force sense display section 162 and the second force sense display section 163 are both surrounded by the same rectangular frames. Alternatively, the first force sense display section 162 and the second force sense display section 163 may have frames different in shape from each other or may have frames having shapes other than the rectangular shape. The shape of the frame is not specifically limited. Also, the first force sense display section 162 and the second force sense display section 163 may have frames in the same color or different colors.

The display modes of the first force sense display section 162 and the second force sense display section 163 of the present variation are similar to the display modes in the first force sense display section 62 and the second force sense display section 63 of the first embodiment, and thus the description thereof is omitted.

For the above-described control device 150, the endoscope unit 20 is not an essential element. Therefore, as compared with the medical robot system 1 of the first embodiment, it is easy to use the medical robot system 101 in surgery which does not use the endoscope unit 20.

Second Variation of First Embodiment

Next, a medical robot system according to a second variation of the first embodiment of the present disclosure will be described with reference to FIGS. 10 and 11. The medical robot system and the force sense display device of the present variation have basic configurations similar to those of the first embodiment, but differ from the first embodiment in the number of display devices provided. Accordingly, for the present variation, configuration related to the display of force sense will be described with reference to FIGS. 10 and 11, and other descriptions are omitted.

Figure 10:
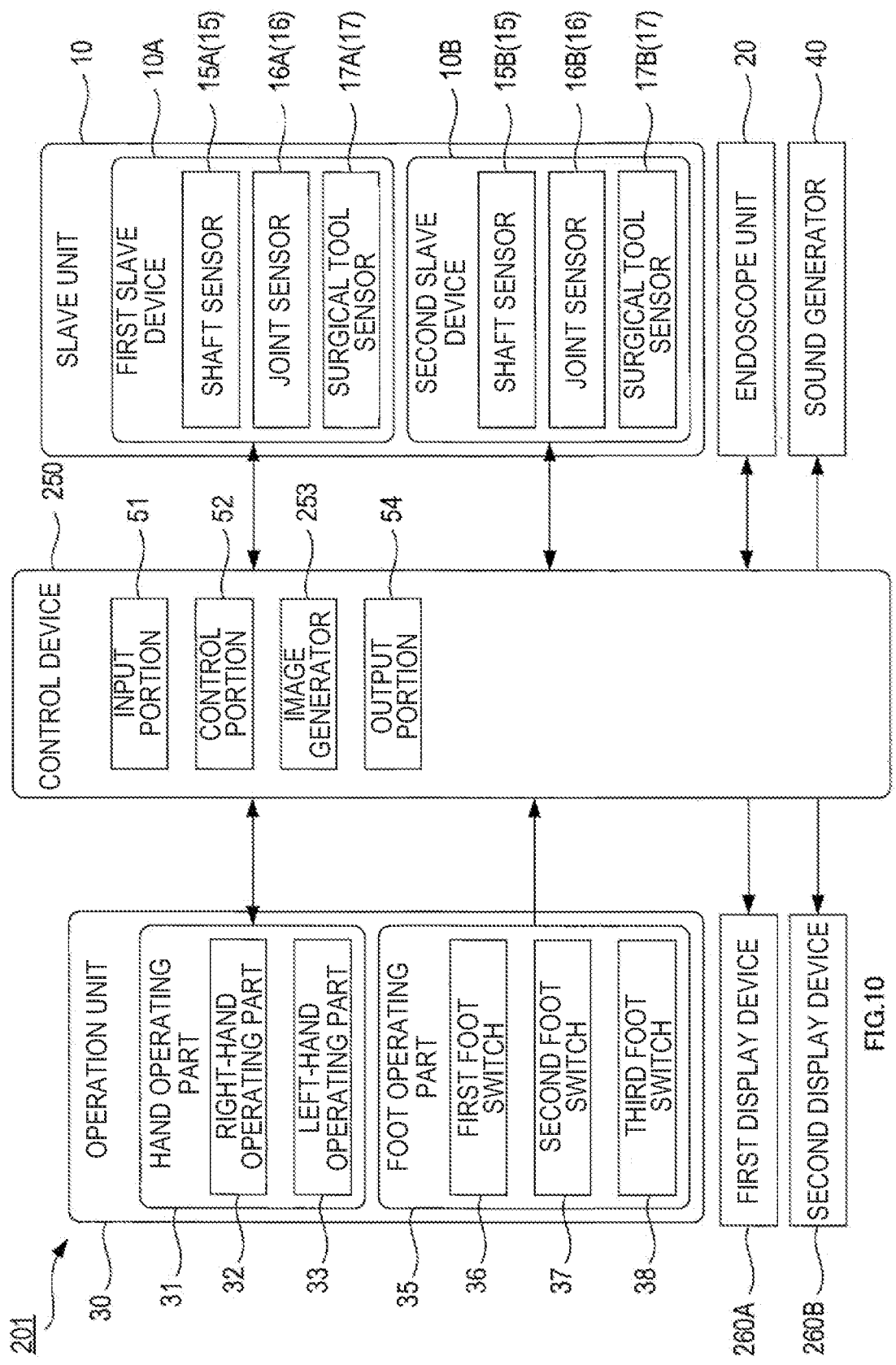
FIG. 10 is a block diagram illustrating a configuration of a medical robot system according to a second variation of the first embodiment of the present disclosure.
Figure 11A:
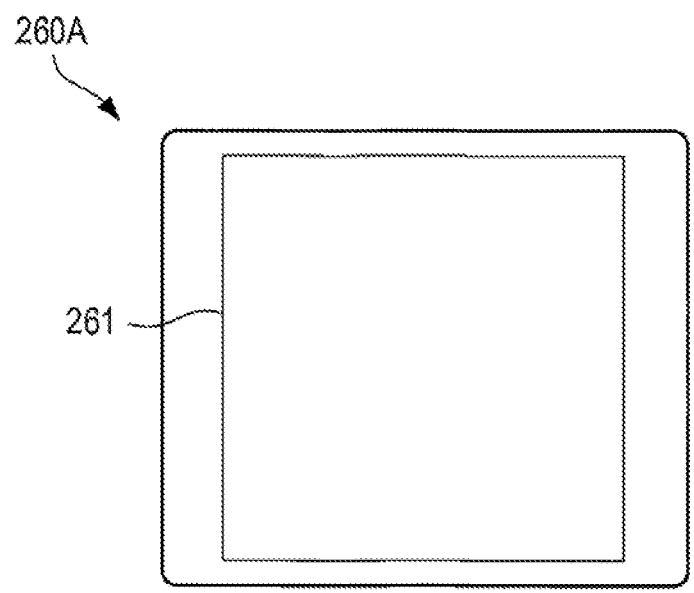
FIG. 11A is a schematic diagram illustrating a mode of display in a first display device.
Figure 11B:
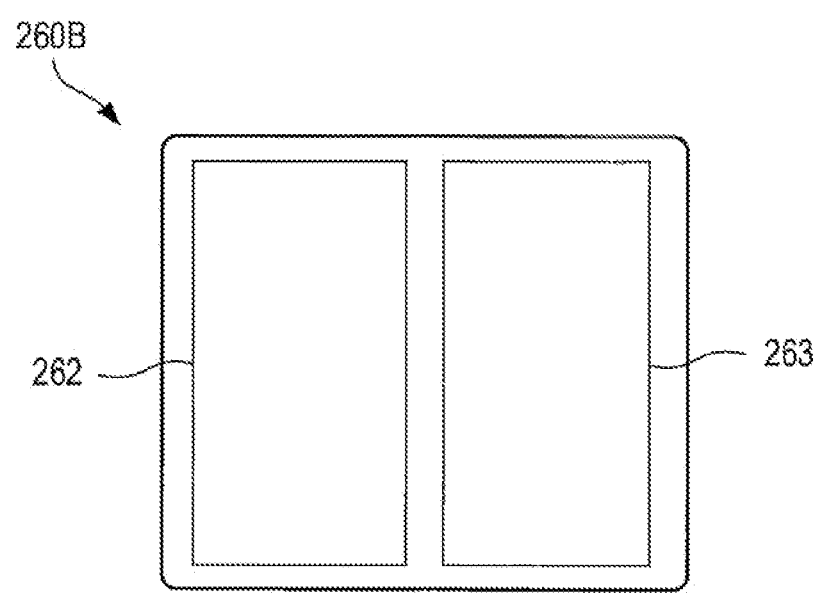
FIG. 11B is a schematic diagram illustrating a mode of display in a second display device.

A medical robot system 201 of the present variation comprises the slave unit 10, the endoscope unit 20, the operation unit 30, the sound generator 40, a control device 250, a first display device 260A, and a second display device 260B, as shown in FIG. 10.

The control device 250 corresponds to the force sense display device, and the first display device 260A and the second display device 260B correspond to an example of the display portion.

The control device 250 controls operation and the like of the slave unit 10 and sound generation in the sound generator 40, and controls contents and modes of displays displayed on the first display device 260A and the second display device 260B.

The control device 250, as shown in FIG. 10, is an information processor such as a computer comprising a CPU, a ROM, a RAM, an input/output interface, and the like. A program stored in a storage device, such as the aforementioned ROM, causes the CPU, the ROM, the RAM, and the input/output interface to cooperate with each other, and function as at least the input portion 51, the control portion 52, the image generator 253, and the output portion 54.

The control device 250 controls operation and the like of the slave unit 10 and sound generation in the sound generator 40, and controls contents and modes of display displayed on the display device 60.

The image generator 253 generates image information that is information of videos and images to be displayed on the first display device 260A and the second display device 260B. Specifically, the image generator 253 generates the image information based on the signal of video and image inputted from the endoscope unit 20 to be outputted to the first display device 260A. The image generator 253 generates the image information based on the signals inputted from the shaft sensor 15, the joint sensor 16, and the surgical tool sensor 17 to be outputted to the second display device 260B. Detail of the image information will be described later.

The first display device 260A and the second display device 260B display the videos and images based on the image information outputted from the control device 250. The first display device 260A and the second display device 260B display the videos and images to those involved in surgery including an operator of endoscopic surgery. There is no specific limitation in method and configuration of the first display device 260A and the second display device 260B as long as they display the videos and images.

The first display device 260A and the second display device 260B may have the display surfaces of the same size, or one may have a larger display surface than the other. Also, the first display device 260A and the second display device 260B may have the same method and configuration to display video and image, or may have different methods and configurations.

Next, control in the medical robot system 201 having the above configuration will be described. Control by the control device 250 regarding the display of the force sense is similar to the control in the first embodiment, and thus the description thereof is omitted.

The image information generated in the image generator 253 will now be described. Specifically, the modes of display in the first display device 260A and the second display device 260B will be described. FIG. 11 is a schematic diagram illustrating the modes of display by the first display device 260A and the second display device 260B based on the image signal generated by the image generator 253 of the present variation.

The image generator 253, as shown in FIG. 10, arranges an endoscope image display section 261 on a display surface in the first display device 260A. Also, the image generator 253 arranges a first force sense display section 262 on the left side and a second force sense display section 263 on the right side, on the display surface of the second display device 260B that is divided into left and right. The endoscope image display section 261 corresponds to an example of the first display region. Also, the first force sense display section 262 and the second force sense display section 263 correspond to an example of the second display region.

In the present variation, the endoscope image display section 261 is arranged in the first display device 260A, and the first force sense display section 262 and the second force sense display section 263 are arranged in the second display device 260B. Alternatively, the first force sense display section 262 and the second force sense display section 263 may be arranged in the first display device 260A, and the endoscope image display section 261 may be arranged in the second display device 260B.

In the above-described control device 250, the display device where the endoscope image display section 261 is arranged differs from the display device where the first force sense display section 262 and the second force sense display section 263 are arranged. Thus, visibility of endoscope image and visibility of force sense display are easily improved.

Second Embodiment

Next, a medical robot system and a force sense display device according to a second embodiment of the present disclosure will be described with reference to FIGS. 12 to 15. The medical robot system and the force sense display device of the present embodiment have basic configurations similar to those of the first embodiment, but differ from the first embodiment in configuration of the slave unit and mode of force sense display. Accordingly, for the present embodiment, the configuration of the slave unit and the mode of force sense display will be described with reference to FIGS. 12 to 15, and other descriptions are omitted.

Figure 12:
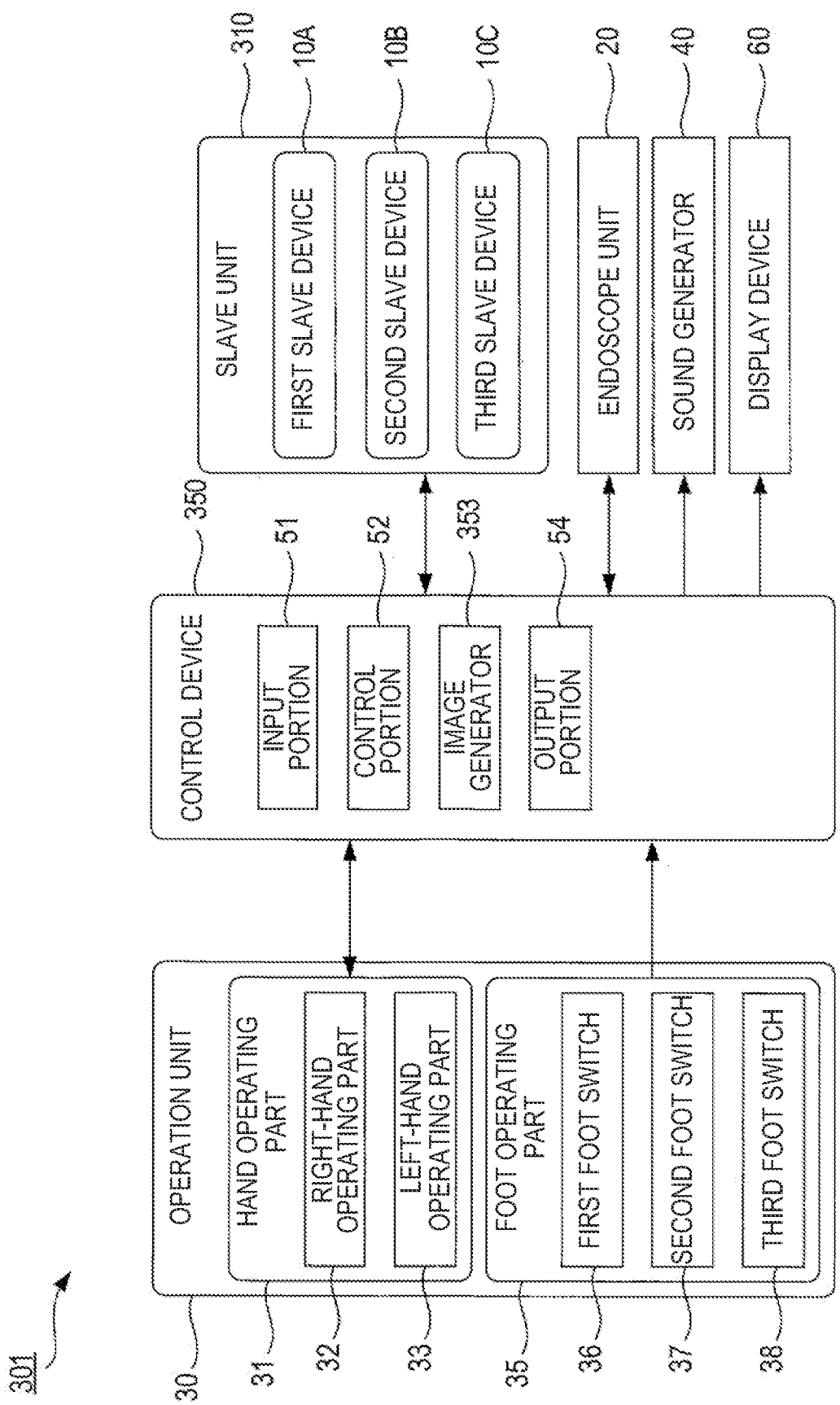
FIG. 12 is a block diagram illustrating a configuration of a medical robot system according to a second embodiment of the present disclosure.

A medical robot system 301 of the present embodiment comprises a slave unit 310, the endoscope unit 20, the operation unit 30, the sound generator 40, a control device 350, and the display device 60, as shown in FIG. 12. The slave unit 310 corresponds to an example of the slave device, and the control device 350 corresponds to an example of the force sense display device.

The slave unit 310, like the slave unit 10 of the first embodiment, supports the surgical tool 14 such as forceps used in endoscopic surgery, and controls at least one of the position and posture of the surgical tool 14 in accordance with the operation inputted to the operation unit 30. In addition, when the surgical tool 14 is forceps, the slave unit 10 opens and closes the forceps.

In the present embodiment, the slave unit 310 includes the first slave device 10A and the second slave device 10B, and a third slave device 10C.

In the present embodiment, the first slave device 10A, the second slave device 10B, and the third slave device 10C are robot arms. Further, the third slave device 10C has the same configuration as those of the first slave device 10A and the second slave device 10B, and supports a similar type of surgical tool 14.

The third slave device 10C, like the first slave device 10A and the second slave device 10B, only needs to be able to control at least one of the position and posture of the surgical tool 14, or open and close forceps as the surgical tool 14. Also, the third slave device 10C need not have an arm-like configuration.

As shown in FIG. 2, the third slave device 10C, like the first slave device 10A and the second slave device 10B, is provided with at least the cartridge 11, the shaft 12, and the joint 13. When it is not necessary to distinguish whether the cartridge 11, the shaft 12, and the joint 13 are provided in the first slave device 10A, in the second slave device 10B, or in the third slave device 10C, these are referred to as cartridge 11, shaft 12, and joint 13.

When it is necessary to distinguish whether the cartridge 11, the shaft 12, and the joint 13 are provided in the first slave device 10A, in the second slave device 10B or in the third slave device 10C, these are referred to as cartridge 11A, shaft 12A, and joint 13A, cartridge 11B, shaft 12B, and joint 13B, or cartridge 11C, shaft 12C, and joint 13C, respectively.

Figure 13:
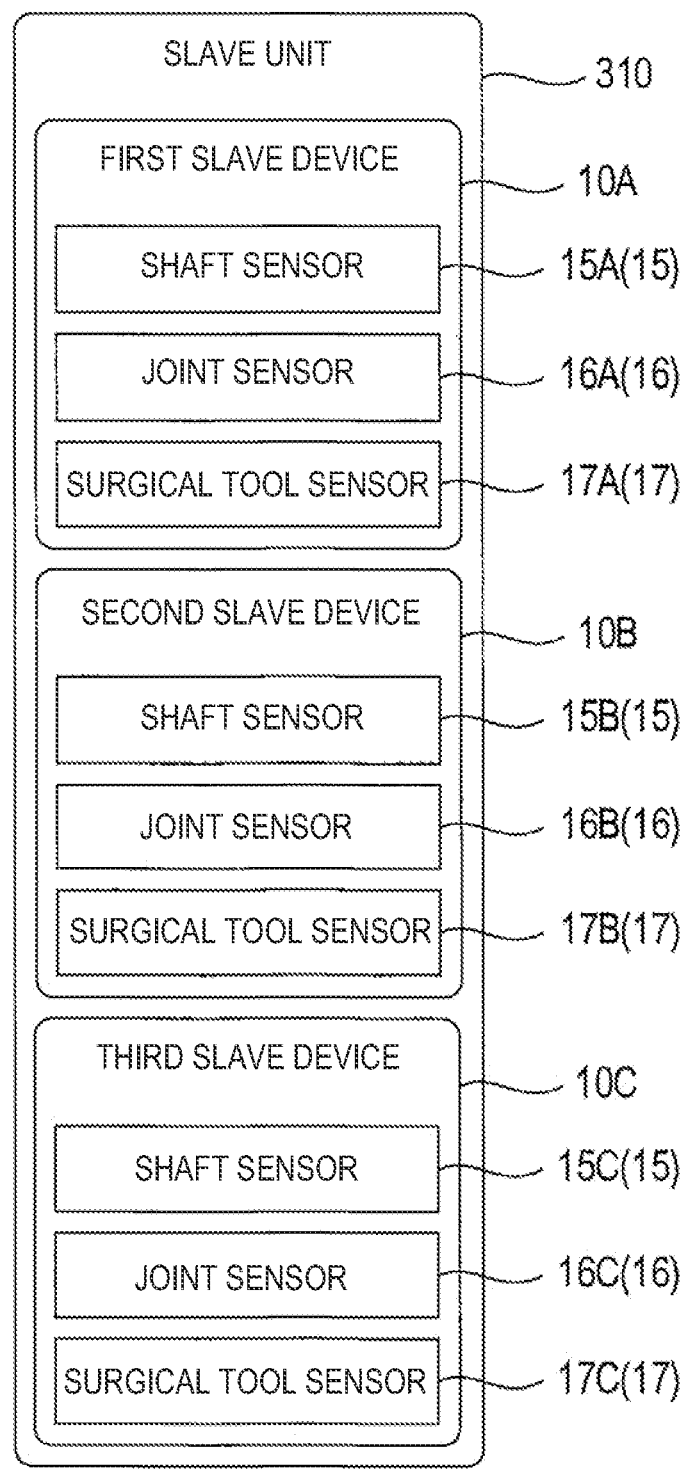
FIG. 13 is a block diagram illustrating a configuration of a slave unit of FIG. 12.

Further, as shown in FIG. 13, the third slave device 10C, like the first slave device 10A and the second slave device 10B, is provided with the shaft sensor 15 that measures an external force applied to the shaft 12, the joint sensor 16 that measures an external force applied to the joint 13, and the surgical tool sensor 17 that measures opening and closing forces applied to the outside by the forceps as the surgical tool 14.

When the shaft sensor 15, the joint sensor 16, and the surgical tool sensor 17 provided in the third slave device 10C are distinguished, these sensors are referred to as shaft sensor 15C, joint sensor 16C, and surgical tool sensor 17C.

The control device 350 controls operation and the like of the slave unit 310 and sound generation in the sound generator 40, and controls contents and modes of display displayed on the display device 60.

The control device 350, as shown in FIG. 12, is an information processor such as a computer comprising a CPU, a ROM, a RAM, an input/output interface and the like. A program stored in a storage device, such as the aforementioned ROM, causes the CPU, the ROM, the RAM, and the input/output interface to cooperate with each other, and function as at least the input portion 51, the control portion 52, an image generator 353, and the output portion 54.

The image generator 353 generates image information that is information of video and image to be displayed on the display device 60. Specifically, the image generator 353 generates the image information based on the signal of video and image inputted from the endoscope unit 20, and the signals inputted from the shaft sensor 15, the joint sensor 16, and the surgical tool sensor 17. Detail of the image information will be described later.

Next, control in the medical robot system 301 having the above configuration will be described. Control by the control device 350 regarding the display of force sense is similar to the control in the first embodiment, and thus the description thereof is omitted.

Figure 14:
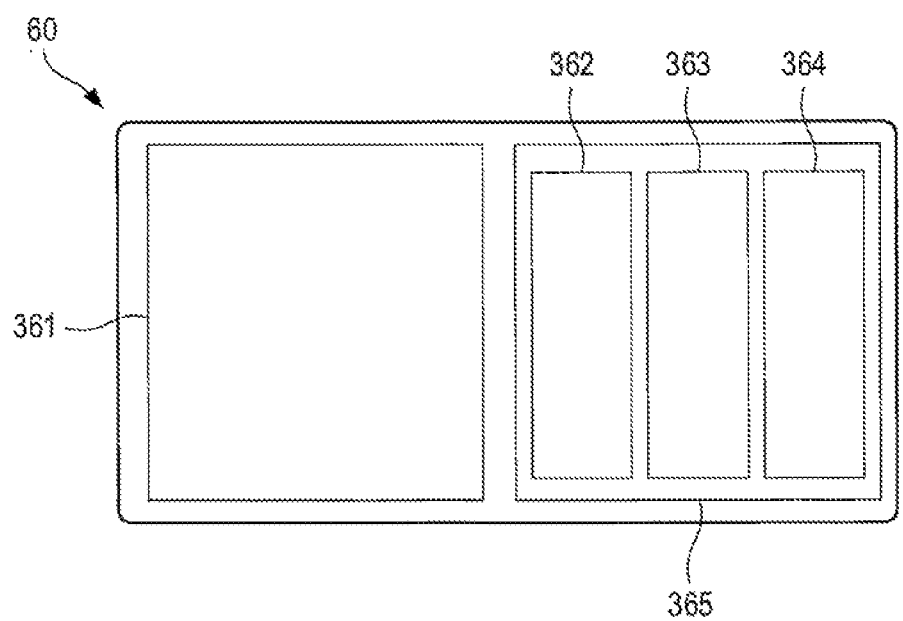
FIG. 14 is a schematic diagram illustrating a mode of display in a display device of FIG. 12.

The image information generated in the image generator 353 will now be described. Specifically, the mode of display in the display device 60 will be described. FIG. 14 is a schematic diagram illustrating the mode of display displayed by the display device 60 based on the image signal generated by the image generator 353 of the present variation.

The image generator 353, as shown in FIG. 14, arranges an endoscope image display section 361 on the left and a force sense display section 365 on the right in a right-left direction on the display surface of the display device 60. Inside the force sense display section 365, a first force sense display section 362, a second force sense display section 363, and a third force sense display section 364 are arranged in an order from left to right.

The endoscope image display section 361 corresponds to an example of the first display region, the force sense display section 365 corresponds to an example of the second display region, and the first force sense display section 362, the second force sense display section 363, and the third force sense display section 364 each correspond to an example of a sub-region.

The endoscope image display section 361 is a region having a larger area than the first force sense display section 362, the second force sense display section 363, and the third force sense display section 364. The image generator 353 generates image information for displaying the information of the video or image inputted from the endoscope unit 20 in the endoscope image display section 361.

The first force sense display section 362, the second force sense display section 363, and the third force sense display section 364 are regions arranged inside the force sense display section 365. The first force sense display section 362, the second force sense display section 363, and the third force sense display section 364 are regions having narrower areas than the endoscope image display section 361. The image generator 353 generates the image information based on the signals inputted from the shaft sensor 15, the joint sensor 16, and the surgical tool sensor 17.

The first force sense display section 362, the second force sense display section 363, and the third force sense display section 364 are partitioned from other regions by frames. Inside the partitioned first force sense display section 362, second force sense display section 363, and third force sense display section 364, displays are performed based on the signals inputted from the shaft sensor 15, the joint sensor 16, and the surgical tool sensor 17. The first force sense display section 362, the second force sense display section 363, and the third force sense display section 364 of the present embodiment have frames formed in the same rectangular shapes. The first force sense display section 362 and the second force sense display section 363 have the frames of the same color, and the third force sense display section 364 has the frame of different color than those of the first force sense display section 362 and the second force sense display section 363. Display modes in the first force sense display section 362, the second force sense display section 363, and the third force sense display section 364 will be described later.

In the present embodiment, the first force sense display section 362 is a region where the display is performed based on the signals inputted from the shaft sensor 15, the joint sensor 16, and the surgical tool sensor 17 corresponding to the first slave device 10A. The second force sense display section 363 is a region where the display is performed based on the signals inputted from the shaft sensor 15, the joint sensor 16, and the surgical tool sensor 17 corresponding to the second slave device 10B. The third force sense display section 364 is a region where the display is performed based on the signals inputted from the shaft sensor 15, the joint sensor 16, and the surgical tool sensor 17 corresponding to the third slave device 10C.

Next, the display modes in the first force sense display section 362, the second force sense display section 363, and the third force sense display section 364 will be described. Since the display modes in the first force sense display section 362, the second force sense display section 363, and the third force sense display section 364 are the same, the display mode in the first force sense display section 362 will be described as a representative example, and description of the display modes in the second force sense display section 363 and the third force sense display section 364 is omitted.

In the present embodiment, in order to easily distinguish between the first force sense display section 362, the second force sense display section 363, and the third force sense display section 364, a title Left Arm is displayed in the first force sense display section 362, a title Right Arm is displayed in the second force sense display section 363, and a title Third Arm is displayed in the third force sense display section 364.

Figure 15:
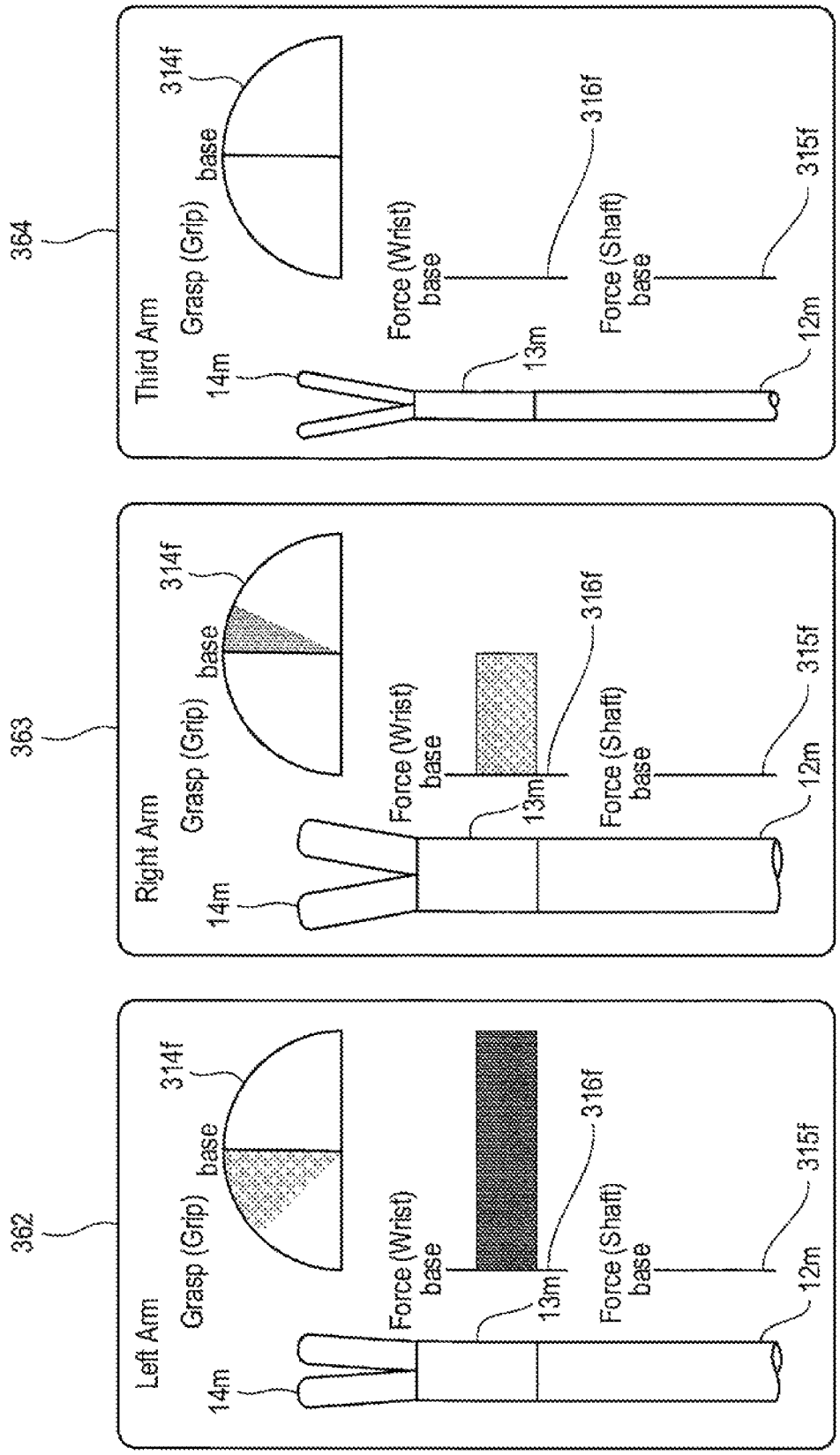
FIG. 15 is a schematic diagram illustrating display modes in a first force sense display section, a second force sense display section, and a third force sense display section of FIG. 14.

The display modes of the first force sense display section 362, the second force sense display section 363, and the third force sense display section 364 are as shown in FIG. 15. In the first force sense display section 362, three-dimensional models of the shaft 12, the joint 13, and the surgical tool 14 of the first slave device 10A are displayed. In other words, a three-dimensional model of shaft 12m, a three-dimensional model of joint 13m, and a three-dimensional model of surgical tool 14m are displayed. The displayed three-dimensional models reflect the actual posture of the shaft 12, and the bent state of the joint 13.

In the second force sense display section 363 and the third force sense display section 364 as well, the three-dimensional models of the shafts 12, the joints 13, and the surgical tools 14 of the second slave device 10B and the third slave device 10C are displayed, respectively.

The shape of the surgical tool 14m in the three-dimensional model is determined based on the type information indicating the type of the surgical tool 14 inputted via the input portion 51. The control device 350 stores the type information indicating the type of the surgical tool 14 and the shape of the surgical tool 14m in the displayed three-dimensional model associated with each other. The image generator 353 acquires information of the shape of the surgical tool 14m associated with the inputted type information, and generates image information for displaying the three-dimensional model.

The type information inputted via the input portion 51 may be information inputted by such as a worker that performs settings of the medical robot system 301 or an operator that performs endoscopic surgery, or may be a detection signal outputted from a sensor that detects the type of the attached surgical tool 14.

At a position adjacent to the shaft 12m in the three-dimensional model, a bar graph 315f showing the magnitude of the force is displayed based on the signal inputted from the shaft sensor 15. In the present embodiment, "Force (Shaft)" is displayed at a position to display the bar graph 315f, and "base" is displayed at a position of a reference line of the bar graph 315f.

Also, at a position adjacent to the joint 13m in the three-dimensional model, a bar graph 316f showing the magnitude of the force is displayed based on the signal inputted from the joint sensor 16. In the present embodiment, "Force (Wrist)" is displayed at a position to display the bar graph 316f, and "base" is displayed at a position of a reference line of the bar graph 316f.

In the present embodiment, the bar graph 315f and the bar graph 316f are graphs that extend laterally, and lengths of the bar graph 315f and the bar graph 316f correspond to the magnitudes of the forces. Also, colors of the bar graph 315f and the bar graph 316f are changed in accordance with the magnitudes of the forces. For example, as the force increases, the colors are changed among green, yellow, and red.

At a position adjacent to the surgical tool 14 in the three-dimensional model, a fan-shaped figure 314f showing the magnitude of the force to close or open the forceps as the surgical tool 14 is displayed based on the signal inputted from the surgical tool sensor 17.

In the present embodiment, the fan-shaped figure 314f is displayed in a semicircular frame. The semicircular frame comprises a frame extending straight in a horizontal direction, and an upwardly convex arc-shaped frame. Also, there is a reference line extending upward from the center of the frame extending in the horizontal direction.

In the present embodiment, the force to close the surgical tool 14 is represented in the grip display mode in which the fan-shaped figure 314f is displayed on the left side of the reference line. Also, the force to open the forceps as the surgical tool 14 is represented in the dissection display mode in which the fan-shaped figure 314f is displayed on the right side of the reference line. The force to close the surgical tool 14 may be represented by displaying the fan-shaped figure 314f on the right side of the reference line, and the force to open the forceps as the surgical tool 14 may be represented by displaying the fan-shaped figure 314f on the left side of the reference line.

The magnitude of the force is represented by an area of the fan-shaped figure 314f. In other words, the magnitude of the force is represented by a magnitude of an opening angle from the reference line. For example, as the force increases, the area of the fan-shaped figure 314f increases. As the force decreases, the area of the fan-shaped figure 314f decreases.

Color of the fan-shaped figure 314f may be changed in accordance with the magnitude of the force. For example, as the force increases, the color is changed among green, yellow, and red. When the force is not measured by the surgical tool sensor 17, only the semicircular frame and the reference line are displayed, and the fan-shaped figure 314f is not displayed.

With the above-described control device 350, inside the first force sense display section 362, the second force sense display section 363, and the third force sense display section 364 respectively provided in accordance with the first slave device 10A, the second slave device 10B, and the third slave device 10C, the external forces measured in the respective slave devices are displayed. Thus, even if there are two or more slave devices, it is easy to grasp which slave device has measured the external force of the displayed information.

The shapes and hues of at least part of the first force sense display section 362, the second force sense display section 363, and the third force sense display section 364 are differentiated in accordance with the first slave device 10A, the second slave device 10B, and the third slave device 10C. Thus, it is easy to grasp which slave device has measured the external force of the displayed information.

The images showing the shapes of the surgical tools 14 gripped by the respective first slave device 10A, second slave device 10B, and third slave device 10C are displayed in the corresponding first force sense display section 362, second force sense display section 363 and third force sense display section 364. Thus, it becomes easy to grasp which slave device gripping which surgical tool 14 has measured the external force of the displayed information.

First Variation of Second Embodiment

Next, a medical robot system according to a first variation of the second embodiment of the present disclosure will be described with reference to FIGS. 16 and 17. The medical robot system and the force sense display device of the present variation have basic configurations similar to those of the second embodiment, but differ from the second embodiment in mode of display in the force sense display section. Accordingly, for the present variation, the mode of display in the force sense display section will be described with reference to FIGS. 16 and 17, and other descriptions are omitted.

Figure 16:
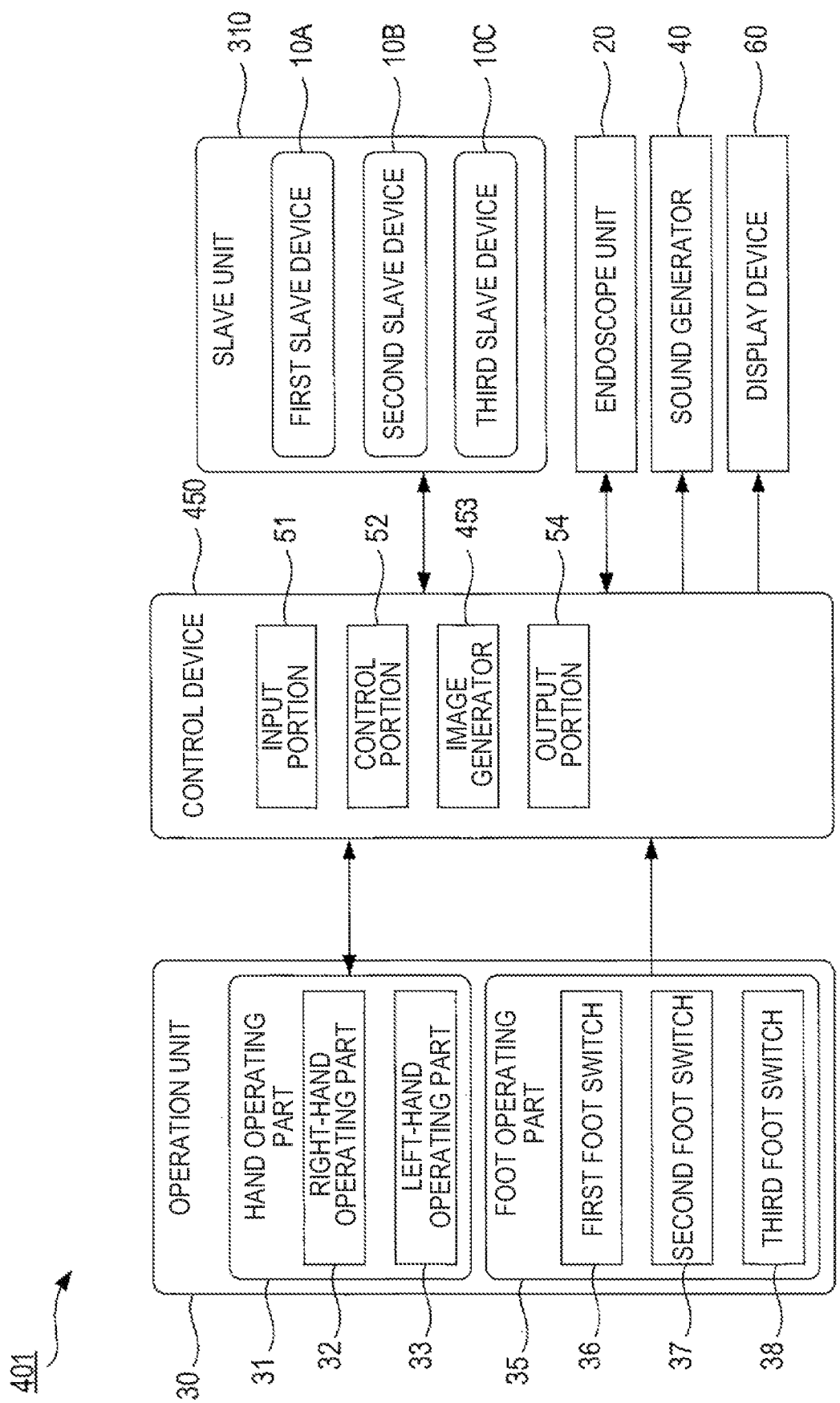
FIG. 16 is a block diagram illustrating a configuration of a medical robot system according to a first variation of the second embodiment of the present disclosure.

A medical robot system 401 of the present embodiment comprises a slave unit 310, the endoscope unit 20, the operation unit 30, the sound generator 40, a control device 450, and the display device 60, as shown in FIG. 16. The control device 450 corresponds to an example of the force sense display device.

The control device 450 controls operation and the like of the slave unit 310 and sound generation in the sound generator 40, and controls contents and modes of display to be displayed on the display device 60.

The control device 450, as shown in FIG. 16, is an information processor such as a computer comprising a CPU, a ROM, a RAM, an input/output interface, and the like. A program stored in a storage device, such as the aforementioned ROM, causes the CPU, the ROM, the RAM, and the input/output interface to cooperate with each other, and function as at least the input portion 51, the control portion 52, an image generator 453, and the output portion 54.

The image generator 453 generates image information that is information of video and image to be displayed on the display device 60. Specifically, the image generator 453 generates the image information based on the signal of video and image inputted from the endoscope unit 20, and the signals inputted from the shaft sensor 15, the joint sensor 16, and the surgical tool sensor 17. Detail of the image information will be described later.

Next, control in the medical robot system 401 having the above configuration will be described. Control by the control device 450 regarding the display of force sense is similar to the control in the first embodiment, and thus the description thereof is omitted. Also, the mode of display in the display device 60 is similar to that in the second embodiment, and thus the description thereof is omitted.

Next, the display modes in the first force sense display section 362, the second force sense display section 363, and the third force sense display section 364 will be described. Since the display modes in the first force sense display section 362, the second force sense display section 363, and the third force sense display section 364 are the same, the display mode in the first force sense display section 362 will be described as a representative example, and description of the display modes in the second force sense display section 363 and the third force sense display section 364 is omitted.

Figure 17:
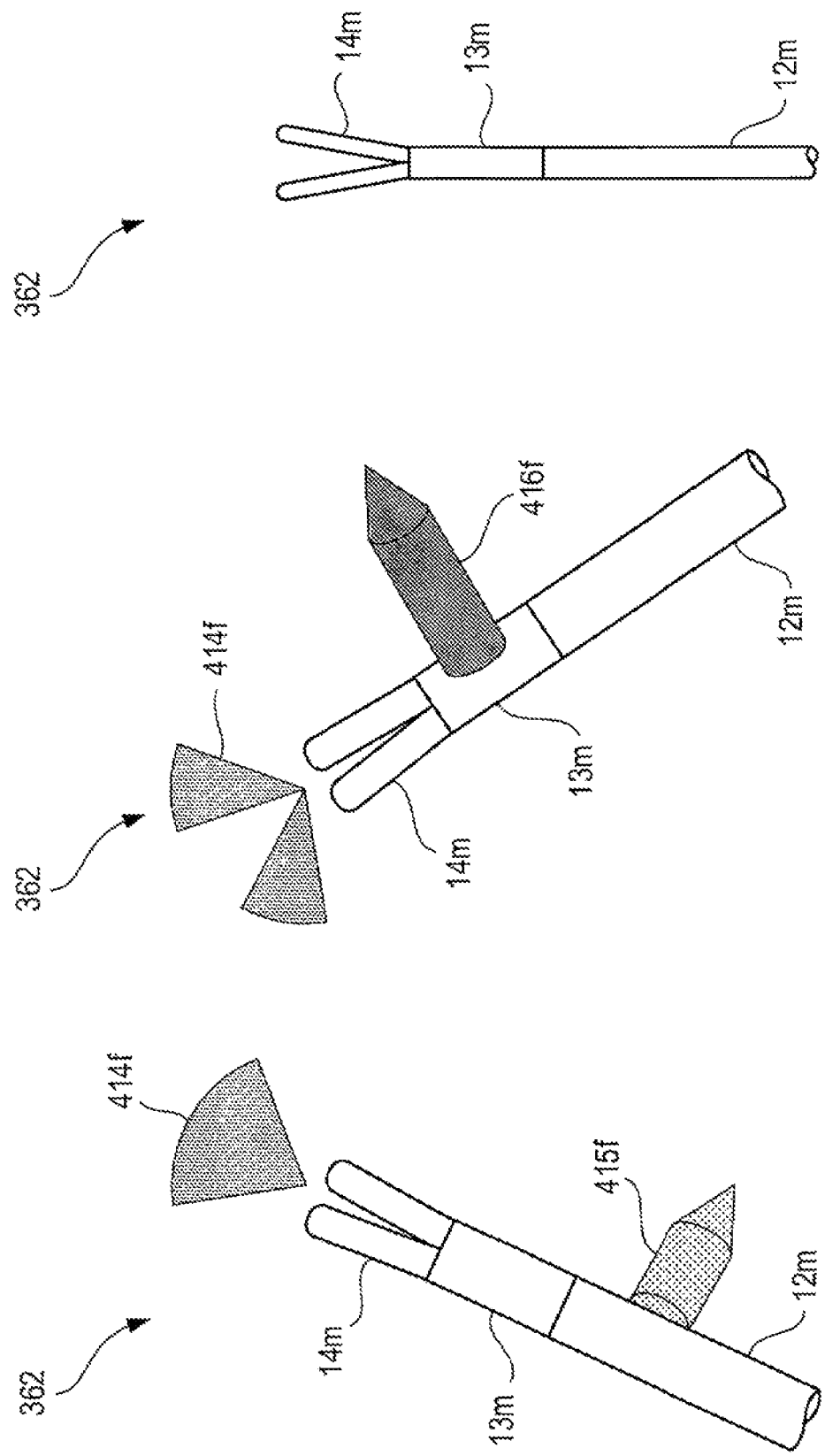
FIG. 17 is a schematic diagram illustrating display modes in a first force sense display section, a second force sense display section, and a third force sense display section in a display device of FIG. 16.

The display modes of the first force sense display section 362, the second force sense display section 363, and the third force sense display section 364 are as shown in FIG. 17. In the first force sense display section 362, three-dimensional models of the shaft 12, the joint 13, and the surgical tool 14 of the first slave device 10A are displayed. In other words, a three-dimensional model of shaft 12m, a three-dimensional model of joint 13m, and a three-dimensional model of surgical tool 14m are displayed. The displayed three-dimensional models reflect the actual posture of the shaft 12, and the actual bent state of the joint 13.

In the second force sense display section 363 and the third force sense display section 364 as well, three-dimensional models of the shafts 12, the joints 13, and the surgical tools 14 of the second slave device 10B and the third slave device 10C are displayed, respectively.

At the shaft 12m in the three-dimensional model, a cylinder graph 415f with a conical tip showing the magnitude of the force and the direction of the force is displayed based on the signal inputted from the shaft sensor 15.

Also, at the joint 13m in the three-dimensional model, a cylinder graph 416f with a conical tip showing the magnitude of the force and the direction of the force is displayed based on the signal inputted from the joint sensor 16.

In the present embodiment, lengths of the cylinder graph 415f and the cylinder graph 416f correspond to the magnitudes of the forces, and the directions in which the cylinder graph 415f and the cylinder graph 416f extend correspond to the directions of the forces. Also, colors of the cylinder graph 415f and the cylinder graph 416f may be changed in accordance of the magnitudes of the forces. For example, as the force increases, the color may be changed among green, yellow, and red.

At a position adjacent to the surgical tool 14 in the three-dimensional model, a fan-shaped figure 414f showing the magnitude of the force to close or open the forceps as the surgical tool 14 is displayed based on the signal inputted from the surgical tool sensor 17.

In the present embodiment, the force to close the surgical tool 14 is represented in the grip display mode in which one fan-shaped figure 414f is displayed. Also, the force to open the forceps as the surgical tool 14 is represented in the dissection display mode in which the fan-shaped figure 414f split in two are displayed.

Further, the fan-shaped figure 414f may be displayed to include a reference line when the number of the fan-shaped figure 414f to be displayed is one. When the number of the fan-shaped figures 414f is two, the fan-shaped figures 414f may be displayed to be spaced apart across the reference line.

The magnitude of the force is represented by an area of the fan-shaped figure 414f. For example, as the force increases, the area of the fan-shaped figure 414f is increased. As the force decreases, the area of the fan-shaped figure 414f is decreased.

Alternatively, color of the fan-shaped figure 414f may be changed in accordance with the magnitude of the force. For example, as the force increases, the color is changed among green, yellow, and red. When the force is not measured by the surgical tool sensor 17, the fan-shaped figure 414f is not displayed.

With the above-described control device 450, visual recognition of information becomes easy since whether the displayed information relates to the gripping force or to the dissecting force is known from whether the number of fan-shaped figures 414f is one or two. Also, the area of the fan-shaped figure 414f is displayed as the magnitude of the gripping force or the dissecting force. Thus, visual recognition of the magnitude of the gripping force or the dissecting force is easy.

Further, when the number of the displayed fan-shaped figures 414f is one, the fan-shaped figure 414f is displayed to include the reference line, and, when the number of the displayed fan-shaped figures 414f is two, the fan-shaped figures 414f are displayed to be spaced apart across the reference line. Thus, visual recognition of the information is further facilitated.

Second Variation of Second Embodiment

Next, a medical robot system according to a second variation of the second embodiment of the present disclosure will be described with reference to FIGS. 18 and 19. The medical robot system and the force sense display device of the present variation have basic configurations similar to those of the second embodiment, but differ from the second embodiment in mode of display in the force sense display section. Accordingly, for the present variation, the mode of display in the force sense display section will be described with reference to FIGS. 18 and 19, and other descriptions are omitted.

Figure 18:
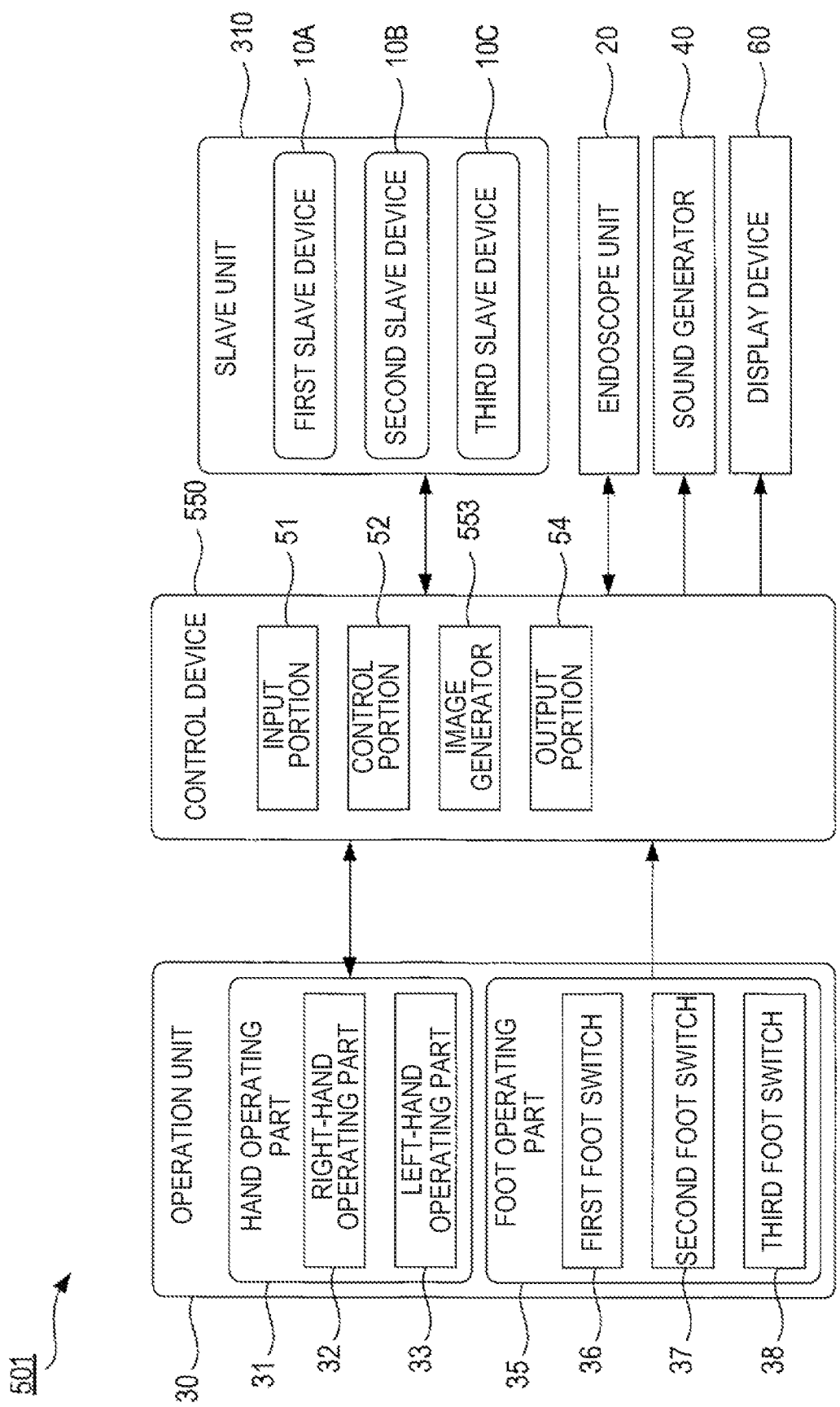
FIG. 18 is a block diagram illustrating a configuration of a medical robot system according to a second variation of the second embodiment of the present disclosure.

A medical robot system 501 of the present embodiment comprises the slave unit 310, the endoscope unit 20, the operation unit 30, the sound generator 40, a control device 550, and the display device 60, as shown in FIG. 18. The control device 550 corresponds to an example of the force sense display device.

The control device 550 controls operation and the like of the slave unit 310 and sound generation in the sound generator 40. Also, the control device 550 controls contents and modes of display displayed on the display device 60.

The control device 550, as shown in FIG. 18, is an information processor such as a computer comprising a CPU, a ROM, a RAM, an input/output interface, and the like. A program stored in a storage device, such as the aforementioned ROM, causes the CPU, the ROM, the RAM, and the input/output interface to cooperate with each other, and function as at least the input portion 51, the control portion 52, an image generator 553, and the output portion 54.

The image generator 553 generates image information that is information of video and image to be displayed on the display device 60. Specifically, the image generator 553 generates the image information based on the signal of video and image inputted from the endoscope unit 20, and the signals inputted from the shaft sensor 15, the joint sensor 16, and the surgical tool sensor 17. Detail of the image information will be described later.

Next, control in the medical robot system 501 having the above configuration will be described. Control by the control device 550 regarding the display of force sense is similar to the control in the first embodiment, and thus the description thereof is omitted. Also, the mode of display in the display device 60 is similar to that in the second embodiment, and thus the description thereof is omitted.

The display modes in the first force sense display section 362, the second force sense display section 363, and the third force sense display section 364 will now be described. Since the display modes in the first force sense display section 362, the second force sense display section 363, and the third force sense display section 364 are the same, the display mode in the first force sense display section 362 will be described as a representative example, and description of the display modes in the second force sense display section 363 and the third force sense display section 364 is omitted.

Figure 19:
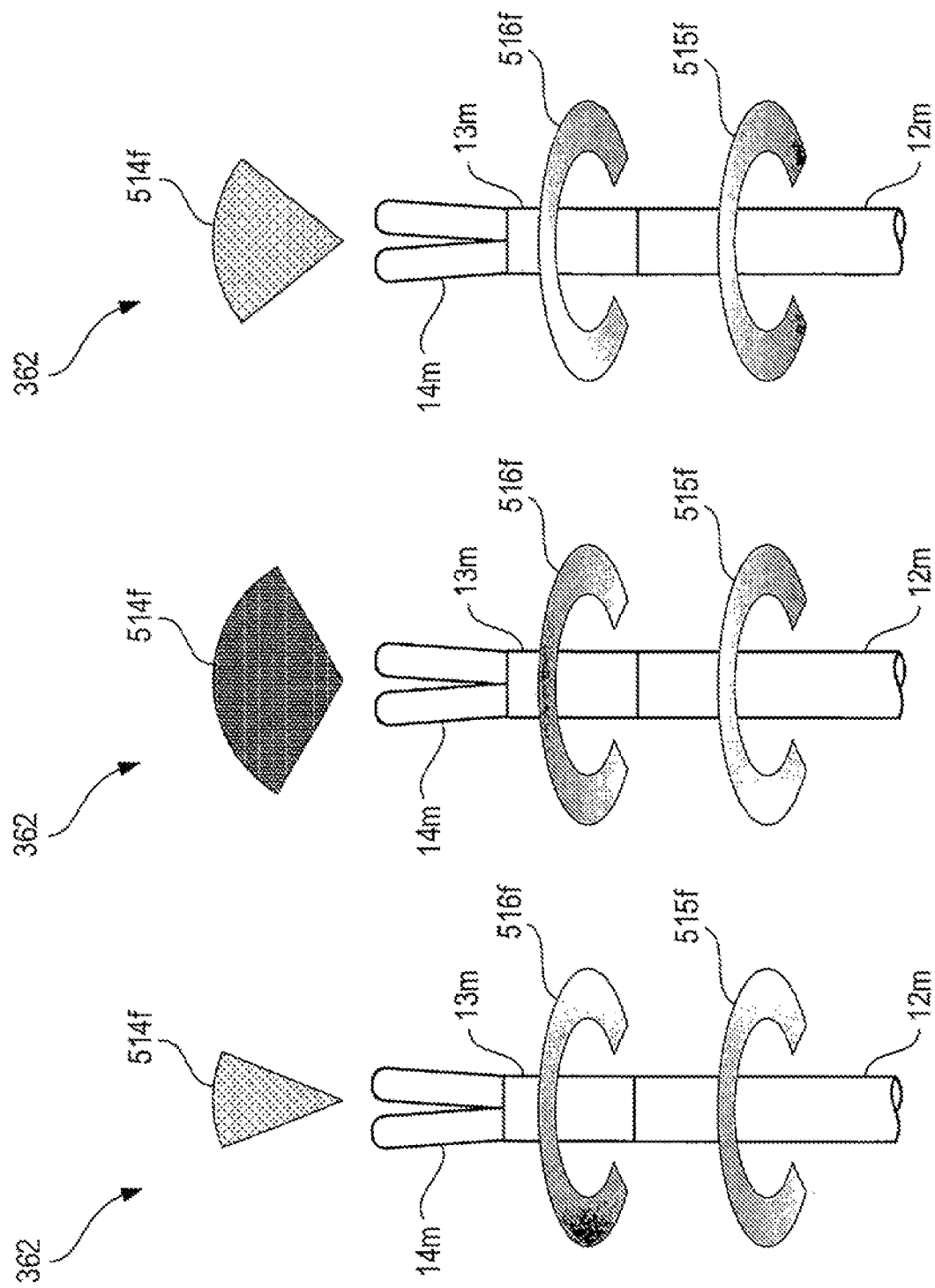
FIG. 19 is a schematic diagram illustrating display modes in a first force sense display section, a second force sense display section, and a third force sense display section in a display device of FIG. 18.

The display modes of the first force sense display section 362, the second force sense display section 363, and the third force sense display section 364 are as shown in FIG. 19. In the first force sense display section 362, three-dimensional models of the shaft 12, the joint 13, and the surgical tool 14 of the first slave device 10A are displayed. In other words, a three-dimensional model of shaft 12m, a three-dimensional model of joint 13m, and a three-dimensional model of surgical tool 14m are displayed. The displayed three-dimensional models reflect the actual posture of the shaft 12, and the actual bent state of the joint 13.

In the second force sense display section 363 and the third force sense display section 364 as well, three-dimensional models of the shafts 12, the joints 13, and the surgical tools 14 of the second slave device 10B and the third slave device 10C are displayed, respectively.

At the shaft 12m in the three-dimensional model, a circular graph 515f showing the magnitude of the force and the direction of the force is displayed based on the signal inputted from the shaft sensor 15.

Also, at the joint 13m in the three-dimensional model, a circular graph 516f showing the magnitude of the force and the direction of the force is displayed based on the signal inputted from the joint sensor 16. In the present embodiment, the circular graph 515f and the circular graph 516f are partially cut out, but may have a shape without cutout.

Also, in the present embodiment, colors displayed in the circular graph 515f and the circular graph 516f correspond to the magnitudes of the forces, and also correspond to the directions in which the forces act. Specifically, in each of the circular graph 515f and the circular graph 516f, the direction in which the force acts is displayed by changing the color of a region corresponding to the direction in which the force acts. Further, as the force increases, the color of the region corresponding to the direction in which the force acts is changed among green, yellow, and red.

At a position adjacent to the surgical tool 14 in the three-dimensional model, a fan-shaped figure 514f showing the magnitude of the force to close or open the forceps as the surgical tool 14 is displayed based on the signal inputted from the surgical tool sensor 17.

In the present embodiment, the force to close the surgical tool 14 is represented in the grip display mode in which the fan-shaped figure 514f is displayed in red. Also, the force to open the forceps as the surgical tool 14 is represented in the dissection display mode in which the fan-shaped figure 514f is displayed in blue.

The magnitude of the force is represented by an area of the fan-shaped figure 514f. For example, as the force increases, the area of the fan-shaped figure 514f is increased. As the force decreases, the area of the fan-shaped figure 514f is decreased.

Alternatively, shade of the color of the fan-shaped figure 514f may be changed in accordance with the magnitude of the force. For example, as the force increases, the color becomes darker. As the force decreases, the color becomes lighter. When the force is not measured by the surgical tool sensor 17, the fan-shaped figure 514f is not displayed.

With the above-described control device 550, visual recognition of information becomes easy since the fan-shaped figure 514f is displayed with different colors or hues. For example, it becomes possible to confirm the fan-shaped figure 514f displayed in the grip display mode and the dissection display mode by the displayed color or hue.

It becomes easy to grasp the magnitude of the force in the fan-shaped figure 514f by changing the shade of the displayed color or hue based on the magnitude of the force in the fan-shaped figure 514f. Thus, it becomes easy to grasp the magnitude of the displayed gripping force or dissecting force.

Third Variation of Second Embodiment

Next, a medical robot system according to a third variation of the second embodiment of the present disclosure will be described with reference to FIGS. 20 and 21. The medical robot system and the force sense display device of the present variation have basic configurations similar to those of the second embodiment, but differ from the second embodiment in mode of display in the force sense display section. Accordingly, for the present variation, the mode of display in the force sense display section will be described with reference to FIGS. 20 and 21, and other descriptions are omitted.

Figure 20:
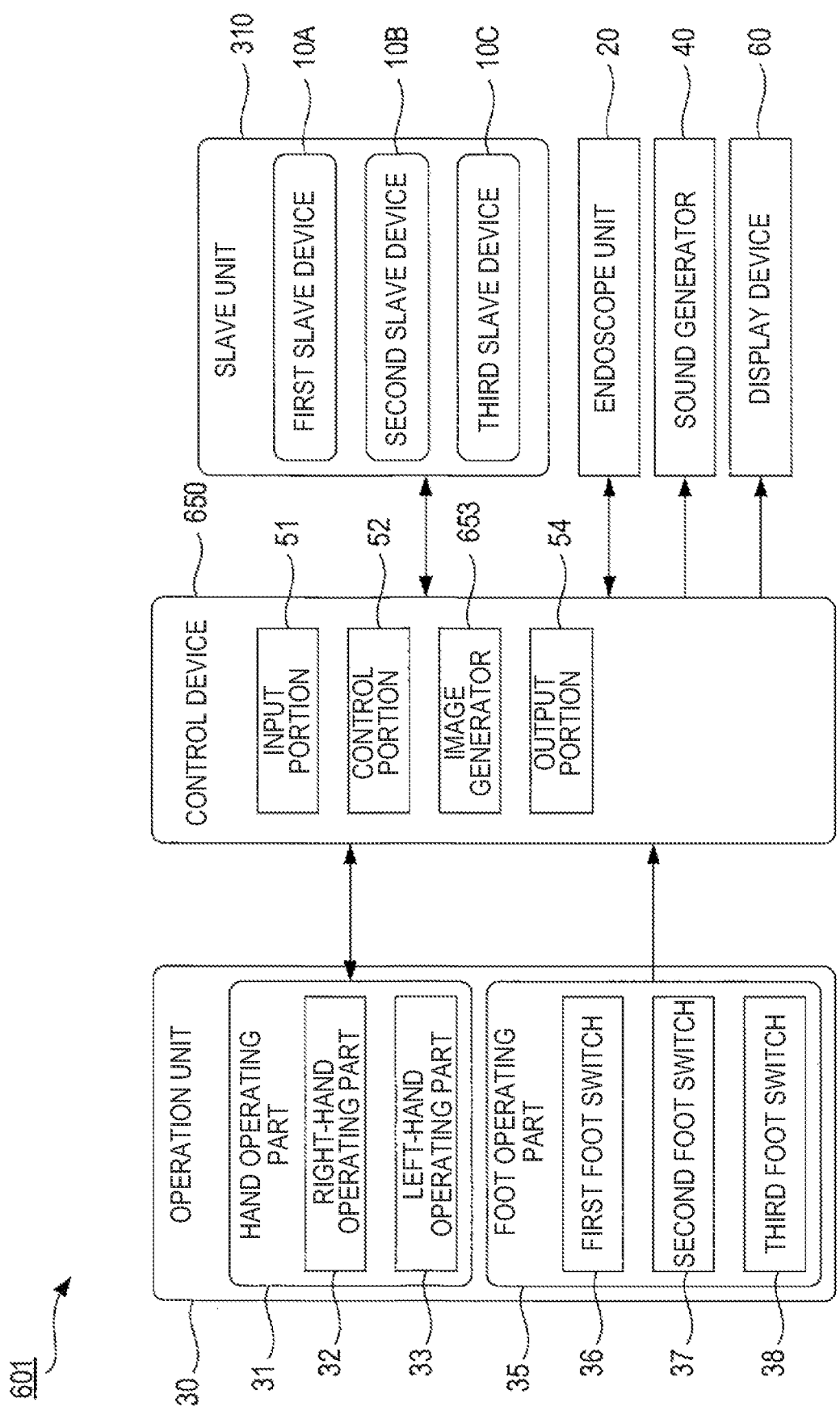
FIG. 20 is a block diagram illustrating a configuration of a medical robot system according to a third variation of the second embodiment of the present disclosure.

A medical robot system 601 of the present embodiment comprises the slave unit 310, the endoscope unit 20, the operation unit 30, the sound generator 40, a control device 650, and the display device 60, as shown in FIG. 20. The control device 650 corresponds to an example of the force sense display device.

The control device 650 controls operation and the like of the slave unit 310 and sound generation in the sound generator 40. Also, the control device 650 controls contents and modes of display displayed on the display device 60.

The control device 650, as shown in FIG. 20, is an information processor such as a computer comprising a CPU, a ROM, a RAM, an input/output interface, and the like. A program stored in a storage device, such as the aforementioned ROM, causes the CPU, the ROM, the RAM, and the input/output interface to cooperate with each other, and function as at least the input portion 51, the control portion 52, an image generator 653, and the output portion 54.

The image generator 653 generates image information that is information of video and image to be displayed on the display device 60. Specifically, the image generator 653 generates the image information based on the signal of video and image inputted from the endoscope unit 20, and the signals inputted from the shaft sensor 15, the joint sensor 16, and the surgical tool sensor 17. Detail of the image information will be described later.

Next, control in the medical robot system 601 having the above configuration will be described. Control by the control device 650 regarding the display of force sense is similar to the control in the first embodiment, and thus the description thereof is omitted. Also, the mode of display in the display device 60 is similar to that in the second embodiment, and thus the description thereof is omitted.

The display modes in the first force sense display section 362, the second force sense display section 363, and the third force sense display section 364 will now be described. Since the display modes in the first force sense display section 362, the second force sense display section 363, and the third force sense display section 364 are the same, the display mode in the first force sense display section 362 will be described as a representative example, and description of the display modes in the second force sense display section 363 and the third force sense display section 364 is omitted.

Figure 21:
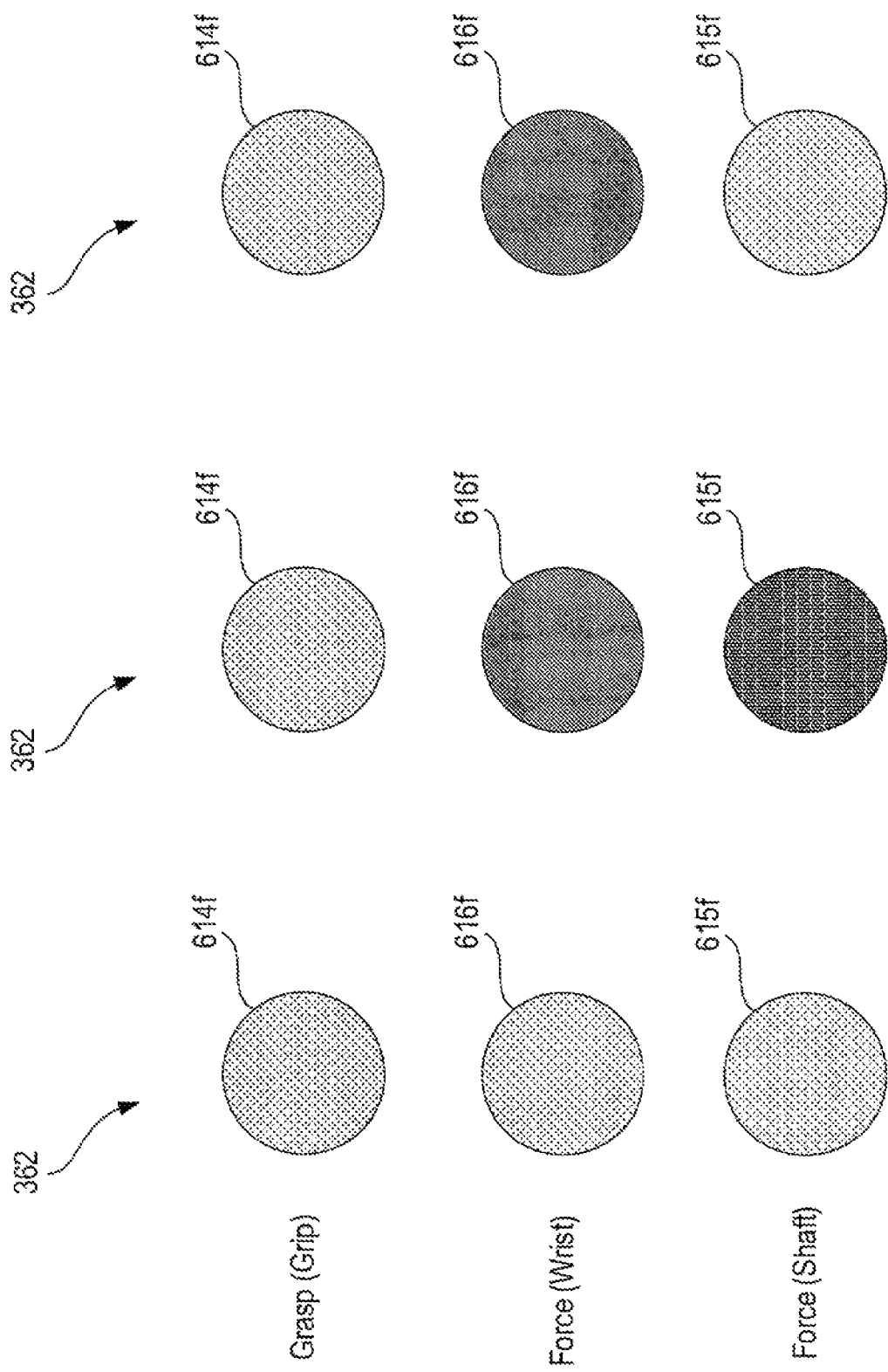
FIG. 21 is a schematic diagram illustrating display modes in a first force sense display section, a second force sense display section, and a third force sense display section in a display device of FIG. 20.

The display modes in the first force sense display section 362, the second force sense display section 363, and the third force sense display section 364 are as shown in FIG. 21. In the lower parts of the first force sense display section 362, the second force sense display section 363, and the third force sense display section 364, circular figures 615$f$ showing the magnitudes of the forces are displayed based on the signals inputted from the shaft sensors 15. In the present embodiment, "Force (Shaft)" is displayed at a position to display the circular figures 615$f$.

In the middle parts of the first force sense display section 362, the second force sense display section 363, and the third force sense display section 364, circular figures 616$f$ showing the magnitudes of the forces are displayed based on the signals inputted from the joint sensors 16. In the present embodiment, "Force (Wrist)" is displayed at a position to display the circular figures 616$f$.

In the upper parts of the first force sense display section 362, the second force sense display section 363, and the third force sense display section 364, circular figures 614$f$ showing the magnitudes of the forces are displayed based on the signals inputted from the surgical tool sensors 17. In the present embodiment, Grip is displayed at a position to display the circular figures 614$f$.

In the present embodiment, colors of the circular figures 615$f$, the circular figures 616$f$, and the circular figures 614$f$ are changed in accordance with the magnitudes of the forces. For example, as the force increases, the color is changed among green, yellow, and red (or orange).

With the above-described control device 650, the magnitude of the value of the external force is represented by the color. Therefore, as compared with the case where the magnitude of the value of the external force is represented by a numerical value, it becomes easy to intuitively grasp the magnitude of the value of the external force.

Fourth Variation of Second Embodiment

Next, a medical robot system according to a fourth variation of the second embodiment of the present disclosure will be described with reference to FIGS. 22 and 23. The medical robot system and the force sense display device of the present variation have basic configurations similar to those of the second embodiment, but differ from the second embodiment in mode of display in the force sense display section. Accordingly, for the present variation, the mode of display in the force sense display section will be described with reference to FIGS. 22 and 23, and other descriptions are omitted.

Figure 22:
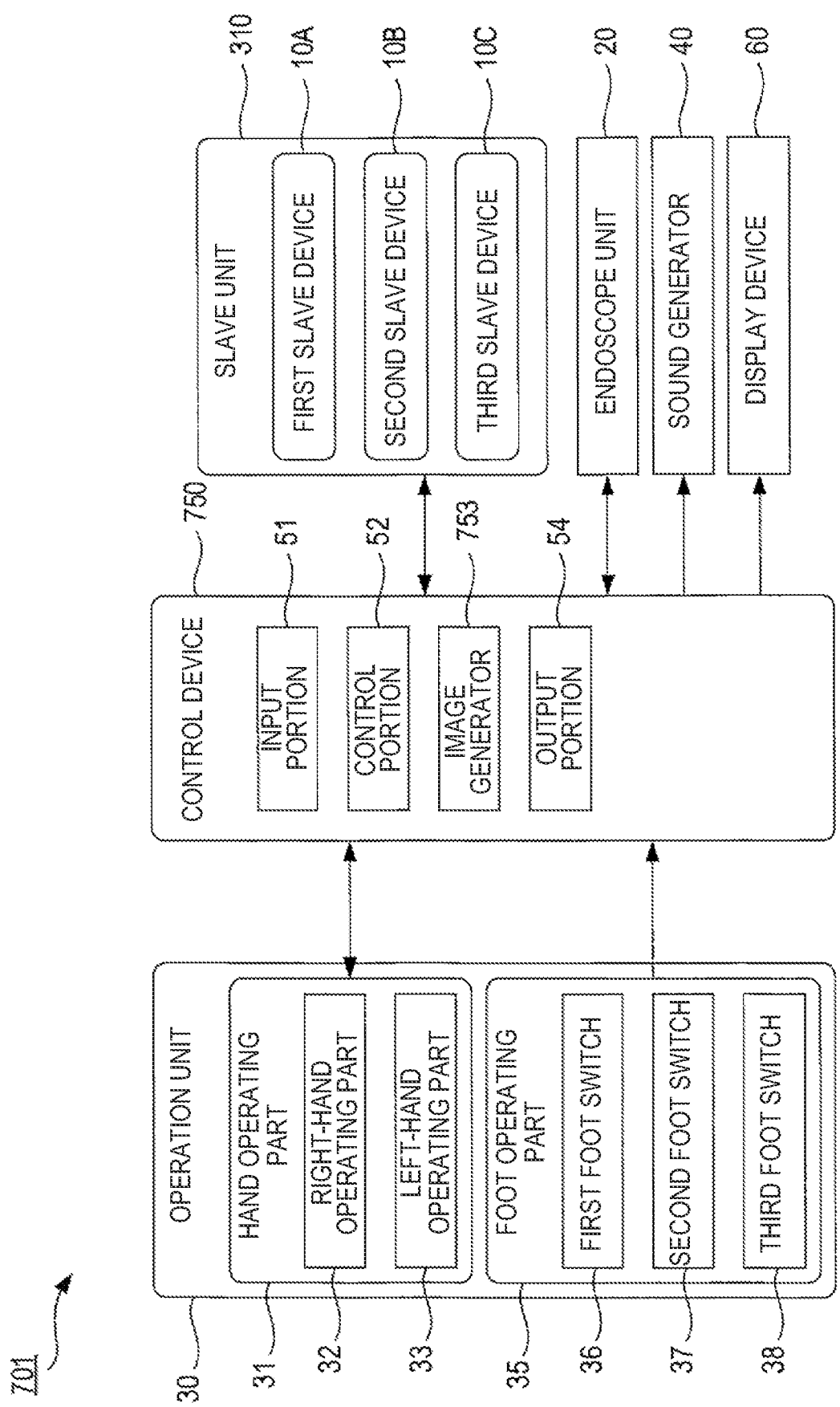
FIG. 22 is a block diagram illustrating a configuration of a medical robot system according to a fourth variation of the second embodiment of the present disclosure.

A medical robot system 701 of the present embodiment comprises the slave unit 310, the endoscope unit 20, the operation unit 30, the sound generator 40, a control device 750, and the display device 60, as shown in FIG. 22. The control device 750 corresponds to an example of the force sense display device.

The control device 750 controls operation and the like of the slave unit 310 and sound generation in the sound generator 40. Also, the control device 750 controls contents and modes of display displayed on the display device 60.

The control device 750, as shown in FIG. 22, is an information processor such as a computer comprising a CPU, a ROM, a RAM, an input/output interface, and the like. A program stored in a storage device, such as the aforementioned ROM, causes the CPU, the ROM, the RAM, and the input/output interface to cooperate with each other, and function as at least the input portion 51, the control portion 52, an image generator 753, and the output portion 54.

The image generator 753 generates image information that is information of video and image to be displayed on the display device 60. Specifically, the image generator 753 generates the image information based on the signal of video and image inputted from the endoscope unit 20, and the signals inputted from the shaft sensor 15, the joint sensor 16, and the surgical tool sensor 17. Detail of the image information will be described later.

Next, control in the medical robot system 701 having the above configuration will be described. Control by the control device 750 regarding the display of force sense is similar to the control in the first embodiment, and thus the description thereof is omitted. Also, the mode of display in the display device 60 is similar to that in the second embodiment, and thus the description thereof is omitted.

The display modes in the first force sense display section 362, the second force sense display section 363, and the third force sense display section 364 will now be described. Since the display modes in the first force sense display section 362, the second force sense display section 363, and the third force sense display section 364 are the same, the display mode in the first force sense display section 362 will be described as a representative example, and description of the display modes in the second force sense display section 363 and the third force sense display section 364 is omitted.

The display modes in the first force sense display section 362, the second force sense display section 363, and the third force sense display section 364 are as shown in FIG. 23. In the lower parts of the first force sense display section 362, the second force sense display section 363, and the third force sense display section 364, pie charts 715f showing the magnitudes of the forces are displayed based on the signals inputted from the shaft sensors 15. In the present embodiment, "Force (Shaft)" is displayed at a position to display the pie charts 715f.

In the middle parts of the first force sense display section 362, the second force sense display section 363, and the third force sense display section 364, pie charts 716f showing the magnitudes of the forces are displayed based on the signals inputted from the joint sensors 16. In the present embodiment, "Force (Wrist)" is displayed at a position to display the pie charts 716f.

In the upper parts of the first force sense display section 362, the second force sense display section 363, and the third force sense display section 364, pie charts 714f showing the magnitudes of the forces are displayed based on the signals inputted from the surgical tool sensor 17. In the present embodiment, Grip is displayed at a position to display the pie charts 714f.

In the present embodiment, areas and colors of the pie charts 715f, the pie charts 716f, and the pie charts 714f are changed in accordance with the magnitudes of the forces. For example, as the force increases, the area of the pie chart is increased and the color is changed among green, yellow, and red (or orange).

With the above-described control device 750, the magnitude of the value of the external force is represented by the color, shape, and area. Therefore, as compared with the case where the magnitude of the value of the external force is represented by a numerical value, it becomes easy to intuitively grasp the magnitude of the value of the external force.

The technical scope of the present disclosure is not limited to the above-described embodiments, and various modifications can be made within the scope not departing from the gist of the present disclosure. For example, the present disclosure is not limited to application to the above-described embodiments or variations but may be applied to an embodiment in which these embodiments and variations are appropriately combined. There is no particular limitation to the application of the present disclosure.

The invention claimed is:

1. A medical robot system comprising:
at least one memory storing computer code; and
at least one central processing unit (CPU) which accesses the at least one memory and executes the computer code to cause the at least one CPU to perform operations comprising:
receiving, from one or more sensors attached to at least one of a surgical tool or a slave device that supports the surgical tool and configured to measure forces at two or more points on the at least one of the surgical tool or the slave device that supports the surgical tool, measurement signals of the forces measured at the two or more points on the at least one of the surgical tool or the slave device that supports the surgical tool;
generating image information for displaying information of the forces as images in association with the two or more points at which the forces are measured, based on the measurement signals; and
outputting the image information that is generated to a display device configured to display the image information for the two or more points in a second display region of the display device which is different from a first display region of the display device in which information on operation of the surgical tool is displayed.

2. The medical robot system according to claim 1, wherein each image represents a respective value of the force by at least one of a color, a shape, or an area of the image.

3. The medical robot system according to claim 1, wherein the slave device comprises a plurality of slave devices, each supporting a respective surgical tool,
the second display region includes a plurality of sub-regions corresponding respectively to the plurality of slave devices,
the at least one CPU receives the measurement signals of the forces measured at the two or more points on each of the plurality of slave devices, and
the at least one CPU generates the image information for displaying the images of the forces for each of the plurality of slave devices in a corresponding one of the plurality of sub-regions.

4. The medical robot system according to claim 3, wherein the plurality of slave devices are identified by a shape and a hue of at least a part of the sub-region.

5. The medical robot system according to claim 4, wherein the at least one CPU receives type information indicating a type of the surgical tool grasped by each of the plurality of slave devices, and
the at least one CPU generates the image information including an image showing a shape of the surgical tool in a sub-region of the plurality of sub-regions that corresponds to the slave device grasping the surgical tool, based on the type information.

6. The medical robot system according to claim 1, wherein the slave device comprises a shaft and the surgical tool is arranged at an end of the shaft,
the slave device comprises a joint that enables a change in a posture of the surgical tool near the end of the shaft,
the measurement signals include a joint measurement signal relating to a force acting on the joint and an arm measurement signal relating to a force acting on a part of the slave device other than the joint,
the forces comprise the force acting on the joint and the force acting on the part other than the joint, and
the at least one CPU generates the image information for displaying information on the force acting on the joint and information on the force acting on the part other than the joint, based on the joint measurement signal and the arm measurement signal.

7. The medical robot system according to claim 6, wherein the measurement signals include a surgical tool measurement signal relating to a force acting on the surgical tool, and
the at least one CPU generates the image information for displaying information on the force acting on the surgical tool based on the surgical tool measurement signal.

8. A force sense display method of a medical robot system, the force sense display method comprising:
receiving, by at least one central processing unit (CPU) from one or more sensors configured to measure forces at two or more points on at least one of a surgical tool or a slave device that supports the surgical tool, measurement signals of the forces measured at the two or more points on the at least one of the surgical tool or the slave device that supports the surgical tool;

generating, by the at least one CPU, image information for displaying information of the forces as images in association with the two or more points at which the forces are measured, based on the measurement signals; and outputting, by the at least one CPU, the image information that is generated to a display portion configured to display the image information for the two or more points in a second display region of a display device which is different from a first display region of the display device in which information on operation of the surgical tool is displayed.

9. An apparatus comprising:

a display device having a first display region in which information on an operation of a surgical instrument is displayed, and a second display region different from the first display region;

at least one memory storing computer code; and at least one central processing unit (CPU) which accesses the at least one memory and executes the computer code to cause the at least one CPU to perform operations comprising:

receiving, from one or more sensors attached of the surgical instrument and configured to measure forces at two or more points on the surgical instrument, measurement signals of the forces acting on the two or more points on the surgical instrument;

generating image information on images corresponding respectively to the forces, each image indicating an associated one of the forces; and outputting the image information for the two or more points to the display device to display the images in the second display region.

10. The apparatus according to claim 9, wherein the surgical instrument comprises a surgical tool and a slave device that supports the surgical tool.

11. The apparatus according to claim 10, wherein the slave device comprises a cartridge, a shaft attached to the cartridge, and a joint, and the joint supports the surgical tool.

12. The apparatus according to claim 9, wherein:

the display device displays an image of the surgical instrument in the second display region, and the images corresponding to the forces acting on the two or more points are displayed in the second display region at positions that correspond to positions of the two or more points on the image of the surgical instrument that is displayed.

13. The apparatus according to claim 9, wherein a value of the force is indicated by at least one of a color, a shape, or an area of the image corresponding to the force.

14. The apparatus according to claim 9, wherein the surgical instrument comprises a plurality of slave devices, each supporting a surgical tool, the second display region includes a plurality of sub-regions corresponding respectively to the plurality of slave devices, the measurement signals comprise forces measured for the plurality of slave devices, and the images associated with the forces for the plurality of slave devices are displayed in corresponding ones of the plurality of sub-regions.

15. The apparatus according to claim 14, wherein each of the plurality of sub-regions is displayed with a different shape and/or a different hue to identify a corresponding one of the plurality of slave devices.

16. The apparatus according to claim 14, wherein the at least one CPU receives, for each of the plurality of slave devices, type information indicating a type of the surgical tool grasped by the slave device, and the image information includes an image showing a shape of the surgical tool in a sub-region of the plurality of sub-regions that corresponds to the slave device grasping the surgical tool, based on the type information.

17. The apparatus according to claim 9, wherein the surgical instrument comprises a slave device comprising a shaft and a joint, and a surgical tool is supported by the slave device at an end of the joint, the measurement signals include a joint measurement signal relating to a force acting on the joint and an arm measurement signal relating to a force acting on a part of the slave device other than the joint, the forces comprise the force acting on the joint and the force acting on the part other than the joint, and the images include an image corresponding to the force acting on the joint and an image corresponding to the force acting on the part other than the joint, based on the joint measurement signal and the arm measurement signal.

18. The apparatus according to claim 9, wherein the surgical instrument comprises a surgical tool and a slave device that supports the surgical tool, the measurement signals include a surgical tool measurement signal relating to a force acting on the surgical tool, and the images include an image corresponding to the force acting on the surgical tool.

* * * * *